US012642487B2

(12) United States Patent
Seidman et al.

(10) Patent No.: US 12,642,487 B2
(45) Date of Patent: Jun. 2, 2026

(54) DETECTOR ASSEMBLIES FOR A WEARABLE MODULE OF AN OPTICAL MEASUREMENT SYSTEM AND INCLUDING SPRING-LOADED LIGHT-RECEIVING MEMBERS

(71) Applicant: HI LLC, Los Angeles, CA (US)

(72) Inventors: Scott Jeremy Seidman, Glenview, IL (US); Jennifer Rines, Carlsbad, CA (US); Ryan Field, Culver City, CA (US); Isai Olvera, South Portland, ME (US)

(73) Assignee: HI LLC, Culver City, CA (US)

( * ) Notice: Subject to any disclaimer, the term of this patent is extended or adjusted under 35 U.S.C. 154(b) by 106 days.

(21) Appl. No.: 18/618,725

(22) Filed: Mar. 27, 2024

(65) Prior Publication Data

US 2024/0237942 A1 Jul. 18, 2024

Related U.S. Application Data

(63) Continuation of application No. 17/176,487, filed on Feb. 16, 2021, now Pat. No. 11,969,259.

(Continued)

(51) Int. Cl.
*A61B 5/00* (2006.01)
*G01J 1/04* (2006.01)
(Continued)

(52) U.S. Cl.
CPC .......... *A61B 5/6803* (2013.01); *A61B 5/0059* (2013.01); *A61B 5/6814* (2013.01);
(Continued)

(58) Field of Classification Search
CPC ... A61B 5/6803; A61B 5/0059; A61B 5/6814; A61B 2562/0238; G01J 1/0425;
(Continued)

(56) References Cited

U.S. PATENT DOCUMENTS 5,853,370 A 12/1998 Chance et al.
6,240,309 B1 * 5/2001 Yamashita ......... A61B 5/14552
600/407

(Continued)

FOREIGN PATENT DOCUMENTS

WO 2005050156 A2 6/2005
WO 2006041997 A2 4/2006
WO 2007048039 A2 4/2007

OTHER PUBLICATIONS

Alayed, et al., Characterization of a Time-Resolved Diffuse Optical Spectroscopy Prototype Using Low-Cost, Compact Single Photon Avalanche Detectors for Tissue Optics Applications, Sensors 2018, 18, 3680; doi:10.3390/s18113680, Oct. 29, 2018.

(Continued)

*Primary Examiner* — Tony Ko
(74) *Attorney, Agent, or Firm* — ALG Intellectual Property, LLC

(57) ABSTRACT

A wearable module for use in an optical measurement system includes a housing and a plurality of light-receiving members. The housing includes a target-side surface configured to face a surface of a body of a user when the wearable module is worn by the user. The plurality of light-receiving members protrude from the target-side surface of the housing and are configured to receive photons scattered by a target within the body of the user and guide the received photons toward a photodetector. An extent to which each of the plurality of light-receiving members protrudes from the target-side surface is adjustable such that, when the wearable module is worn by the user, each of the plurality of light-receiving members is in physical contact with the surface of the body.

23 Claims, 20 Drawing Sheets

Related U.S. Application Data

(60) Provisional application No. 63/038,468, filed on Jun. 12, 2020, provisional application No. 62/992,559, filed on Mar. 20, 2020, provisional application No. 62/979,866, filed on Feb. 21, 2020.

(51) Int. Cl.
| | |
|---|---|
| *G01J 1/42* | (2006.01) |
| *G01J 1/44* | (2006.01) |
| *G06F 3/01* | (2006.01) |

(52) U.S. Cl.
CPC ........... *G01J 1/0425* (2013.01); *G01J 1/4228* (2013.01); *G01J 1/44* (2013.01); *G06F 3/015* (2013.01); *A61B 2562/0238* (2013.01); *G01J 2001/4466* (2013.01)

(58) Field of Classification Search
CPC .... G01J 1/4228; G01J 1/44; G01J 2001/4466; G06F 3/015
See application file for complete search history.

(56) References Cited

U.S. PATENT DOCUMENTS

| | | | |
|---|---|---|---|
| 6,384,663 B2 | 5/2002 | Cova et al. | |
| 6,542,763 B1 | 4/2003 | Yamashita et al. | |
| 6,640,133 B2 | 10/2003 | Yamashita et al. | |
| 6,683,294 B1 | 1/2004 | Herbert et al. | |
| 7,356,365 B2 | 4/2008 | Schurman | |
| 7,547,872 B2 | 6/2009 | Niclass et al. | |
| 7,774,047 B2 | 8/2010 | Yamashita et al. | |
| 8,026,471 B2 | 9/2011 | Itzler | |
| 8,078,250 B2 | 12/2011 | Chen et al. | |
| 8,082,015 B2 | 12/2011 | Yodh et al. | |
| 8,518,029 B2 | 8/2013 | Birmingham et al. | |
| 8,633,431 B2 | 1/2014 | Kim | |
| 8,817,257 B2 | 8/2014 | Herve | |
| 9,058,081 B2 | 6/2015 | Baxter | |
| 9,076,707 B2 | 7/2015 | Harmon | |
| 9,131,861 B2 | 9/2015 | Ince et al. | |
| 9,316,735 B2 | 4/2016 | Baxter | |
| 9,401,448 B2 | 7/2016 | Bienfang et al. | |
| 9,419,635 B2 | 8/2016 | Kumar et al. | |
| 9,442,201 B2 | 9/2016 | Schmand et al. | |
| 9,529,079 B1 | 12/2016 | Droz et al. | |
| 9,574,936 B2 | 2/2017 | Heinonen | |
| 9,946,344 B2 | 4/2018 | Ayaz et al. | |
| D817,553 S | 5/2018 | Aaskov et al. | |
| D825,112 S | 8/2018 | Saez | |
| 10,158,038 B1 | 12/2018 | Do et al. | |
| 10,340,408 B1 | 7/2019 | Katnani et al. | |
| 10,424,683 B1 | 9/2019 | Valle et al. | |
| 10,515,993 B2 | 12/2019 | Field et al. | |
| 10,695,167 B2 | 6/2020 | Van Heugten et al. | |
| 10,697,829 B2 | 6/2020 | Delic | |
| 10,772,561 B2 | 9/2020 | Donaldson | |
| 10,809,796 B2 | 10/2020 | Armstrong-Muntner et al. | |
| 10,912,504 B2 | 2/2021 | Nakaji et al. | |
| 11,006,876 B2 | 5/2021 | Johnson et al. | |
| 11,006,878 B2 | 5/2021 | Johnson et al. | |
| 11,857,348 B2 | 1/2024 | Field et al. | |
| 11,903,676 B2 | 2/2024 | Sorgenfrei et al. | |
| 11,950,879 B2 | 4/2024 | Field et al. | |
| 2007/0083097 A1 | 4/2007 | Fujiwara et al. | |
| 2009/0012402 A1 | 1/2009 | Mintz et al. | |
| 2009/0054789 A1* | 2/2009 | Kiguchi ............... | A61B 5/0059 600/476 |
| 2011/0208675 A1 | 8/2011 | Shoureshi et al. | |
| 2013/0342835 A1 | 12/2013 | Blacksberg | |
| 2014/0046152 A1 | 2/2014 | Bechtel et al. | |
| 2014/0191115 A1 | 7/2014 | Webster et al. | |
| 2014/0217264 A1 | 8/2014 | Shepard et al. | |
| 2014/0275891 A1 | 9/2014 | Muehlemann et al. | |
| 2015/0038811 A1 | 2/2015 | Asaka et al. | |
| 2015/0041625 A1 | 2/2015 | Dutton et al. | |
| 2015/0054111 A1 | 2/2015 | Niclass et al. | |
| 2015/0077279 A1 | 3/2015 | Song et al. | |
| 2015/0150505 A1 | 6/2015 | Kaskoun et al. | |
| 2015/0327777 A1 | 11/2015 | Kostic et al. | |
| 2015/0364635 A1 | 12/2015 | Bodlovic et al. | |
| 2016/0057369 A1 | 2/2016 | Wolfe et al. | |
| 2017/0030769 A1 | 2/2017 | Clemens et al. | |
| 2017/0031009 A1 | 2/2017 | Davidovic et al. | |
| 2017/0052065 A1 | 2/2017 | Sharma et al. | |
| 2017/0176596 A1 | 6/2017 | Shpunt et al. | |
| 2017/0179173 A1 | 6/2017 | Mandai et al. | |
| 2017/0202518 A1 | 7/2017 | Furman et al. | |
| 2017/0281086 A1 | 10/2017 | Donaldson | |
| 2017/0343384 A1 | 11/2017 | Nakazato et al. | |
| 2017/0363467 A1 | 12/2017 | Clemens et al. | |
| 2017/0367650 A1 | 12/2017 | Wallois et al. | |
| 2018/0014741 A1 | 1/2018 | Chou | |
| 2018/0027196 A1 | 1/2018 | Yang et al. | |
| 2018/0033751 A1 | 2/2018 | Ban et al. | |
| 2018/0039053 A1 | 2/2018 | Kremer et al. | |
| 2018/0070830 A1 | 3/2018 | Sutin et al. | |
| 2018/0070831 A1 | 3/2018 | Sutin et al. | |
| 2018/0089848 A1 | 3/2018 | Yang et al. | |
| 2019/0113385 A1 | 4/2019 | Fukuchi | |
| 2019/0175068 A1 | 6/2019 | Everdell | |
| 2019/0355861 A1 | 11/2019 | Katnani et al. | |
| 2019/0363210 A1 | 11/2019 | Valle et al. | |
| 2019/0388018 A1 | 12/2019 | Horstmeyer et al. | |
| 2020/0044098 A1 | 2/2020 | Azuma et al. | |
| 2020/0060542 A1 | 2/2020 | Alford et al. | |
| 2020/0116838 A1 | 4/2020 | Erdogan et al. | |
| 2020/0196932 A1 | 6/2020 | Johnson et al. | |
| 2020/0253479 A1 | 8/2020 | Nurmikko | |
| 2020/0315510 A1 | 10/2020 | Johnson et al. | |
| 2020/0337624 A1 | 10/2020 | Johnson et al. | |
| 2020/0390358 A1 | 12/2020 | Johnson et al. | |
| 2021/0290066 A1 | 9/2021 | Field et al. | |

OTHER PUBLICATIONS

Ban, et al., Kernel Flow: a high channel count scalable TD-fNIRS system, https://www.spiedigitallibrary.org/conference-proceedings-of-spie Proc. of SPIE vol. 11663, 116630B doi: 10.1117/12.2582888, Mar. 5, 2021.

Ban, et al., Kernel Flow: a high channel count scalable time-domain functional near-infrared spectroscopy system, https://www.spiedigitallibrary.org/journals/Journal-of-Biomedical-Optics on Jan. 18, 2022.

Contini, et al., Photon migration through a turbid slab described by a model based on diffusion approximation. I. Theory, Appl. Opt. 36(19), 4587 (1997).

Di Sieno, et al., Probe-hosted large area silicon photomultiplier and high-throughput timing electronics for enhanced performance time-domain functional near-infrared spectroscopy, Biomed. Opt. Express 11(11), 6389 (2020).

Fishburn, et al., Temporal Derivative Distribution Repair (TDDR): A motion correction method for fNIRS, Neuroimage. Jan. 1, 2019; 184: 171-179. doi:10.1016/j.neuroimage.2018.09.025.

Huppert, et al., HomER: a review of time-series analysis methods for near-infrared spectroscopy of the brain, Appl. Opt. 48(10), D280 (2009).

Kienle, et al., Improved solutions of the steady-state and the time-resolved diffusion equations for reflectance from a semi-infinite turbid medium, J. Opt. Soc. Am. A 14(1), 246 (1997).

Konugolu, et al., Broadband (600-1350 nm) Time-Resolved Diffuse Optical Spectrometer for Clinical Use, IEEE Journal of Selected Topics in Quantum Electronics, vol. 22, No. 3, May/Jun. 2016.

Lacerenza, et al., Wearable and wireless time-domain near-infrared spectroscopy system for brain and muscle hemodynamic monitoring, Biomed. Opt. Express 11(10), 5934 (2020).

Lange, et al., Clinical Brain Monitoring with Time Domain NIRS: A Review and Future Perspectives, Applied Sciences 9(8), 1612 (2019).

(56)　　　　　References Cited

OTHER PUBLICATIONS

Lange, et al., Maestros: A Multiwavelength Time-Domain NIRS System to Monitor Changes in Oxygenation and Oxidation State of Cytochrome-C-Oxidase, IEEE J. Select. Topics Quantum Electron. 25(1), 1-12 (2019).

Martelli, et al., Optimal estimation reconstruction of the optical properties of a two-layered tissue phantom from time-resolved single-distance measurements, Journal of Biomedical Optics 20(11), 115001 (Nov. 2015).

Mora, et al., Fast silicon photomultiplier improves signal harvesting and reduces complexity in time-domain diffuse optics, Opt. Express 23(11), 13937 (2015).

Pifferi, et al., Performance assessment of photon migration instruments: the MEDPHOT protocol, Applied Optics, 44(11), 2104-2114, 2005.

Prahl, Optical Absorption of Hemoglobin, http://omlc.ogi.edu/spectra/hemoglobin/index.html, 1999.

Re, et al., Multi-channel medical device for time domain functional near infrared spectroscopy based on wavelength space multiplexing, Biomed. Opt. Express 4(10), 2231 (2013).

Renna, et al., Eight-Wavelength, Dual Detection Channel Instrument for Near-Infrared Time-Resolved Diffuse Optical Spectroscopy, IEEE J. Select. Topics Quantum Electron. 25(1), 1-11 (2019).

Torricelli, et al., Time domain functional NIRS imaging for human brain mapping, NeuroImage 85, 28-50 (2014).

Wabnitz, et al., Depth-selective data analysis for time-domain fNIRS: moments vs. time windows, Biomed. Opt. Express 11(8), 4224 (2020).

Wabnitz, et al., Performance assessment of time-domain optical brain imagers, part 1: basic instrumental performance protocol, Journal of Biomedical Optics 19(8), 086010 (Aug. 2014).

Wabnitz, et al., Performance assessment of time-domain optical brain imagers, part 2: nEUROPt protocol, Journal of Biomedical Optics 19(8), 086012 (Aug. 2014).

Wojtkiewicz, et al., Self-calibrating time-resolved near infrared spectroscopy, Biomed. Opt. Express 10(5), 2657 (2019).

Zucchelli, et al., Method for the discrimination of superficial and deep absorption variations by time domain fNIRS, 2013 OSA Dec. 1, 2013 | vol. 4, No. 12 | DOI:10.1364/BOE.4.002893 | Biomedical Optics Express 2893, 2013.

"What are the advantages of multiplexing," Blog, FiberWDM, Mar. 28, 2023. Retrieved on May 9, 2014 from https://www.fiberwdm.com/blog/what-are-the-advantages-of-multiplexing_b101.

Blair, Seraphine. "Multiplexing in modern communication: what it is & advantages," Blog, JAK Electronics, Mar. 12, 2024. Retrieved on May 9, 2024 from https://www.jakelectronics.com/blog/multiplexing.

Nandalal, et al., "Multiplexing," IntechOpen, Sep. 4, 2019. Retrieved on May 9, 2014 from https://www.jakelectronics.com/blog/multiplexing.

* cited by examiner

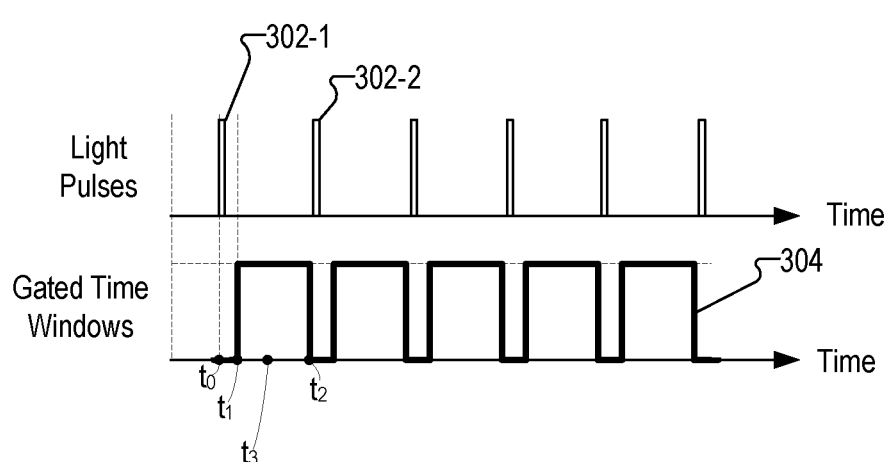
Fig. 3

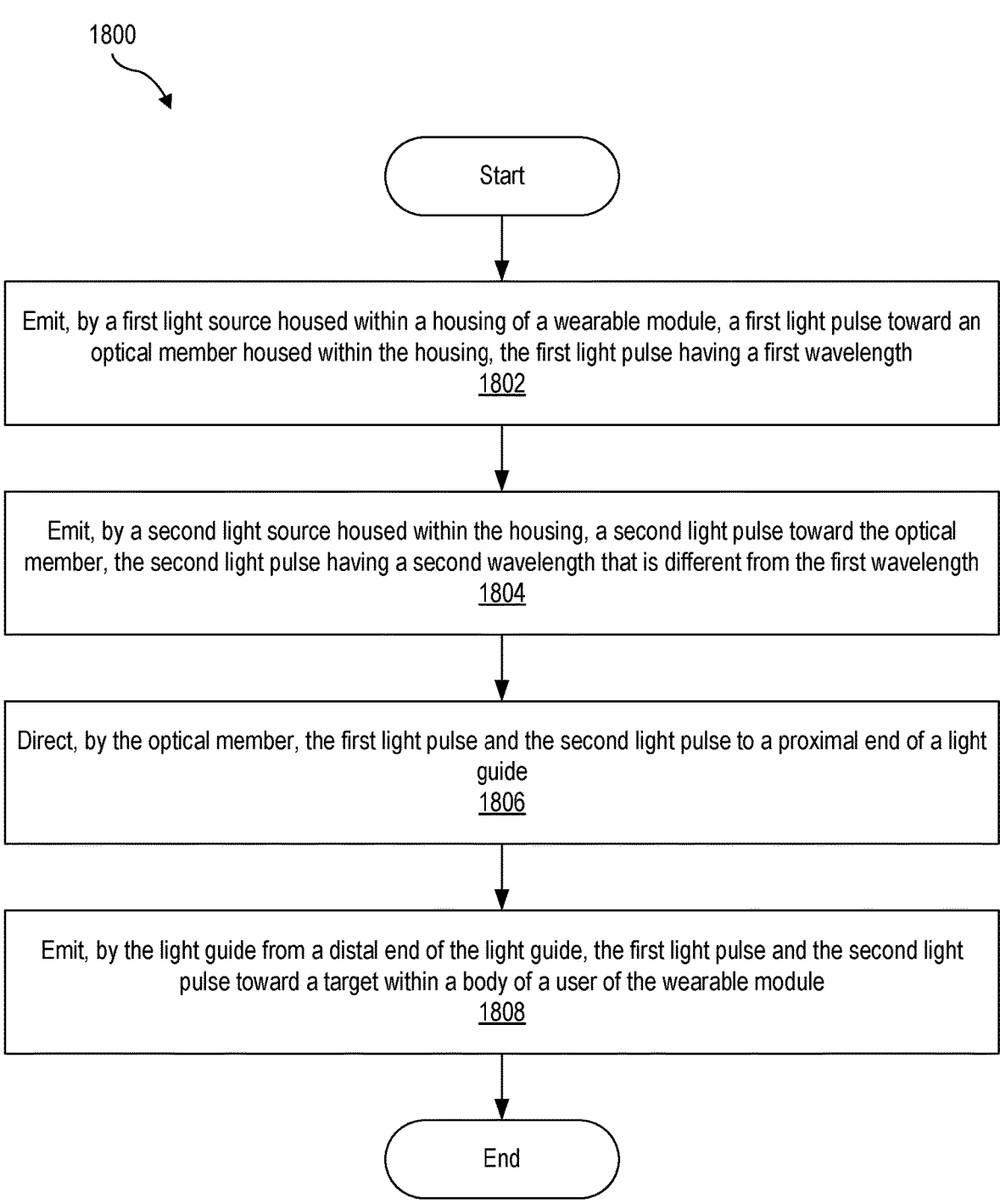

Start

Emit, by a first light source housed within a housing of a wearable module, a first light pulse toward an optical member housed within the housing, the first light pulse having a first wavelength
1802

Emit, by a second light source housed within the housing, a second light pulse toward the optical member, the second light pulse having a second wavelength that is different from the first wavelength
1804

Direct, by the optical member, the first light pulse and the second light pulse to a proximal end of a light guide
1806

Emit, by the light guide from a distal end of the light guide, the first light pulse and the second light pulse toward a target within a body of a user of the wearable module
1808

End

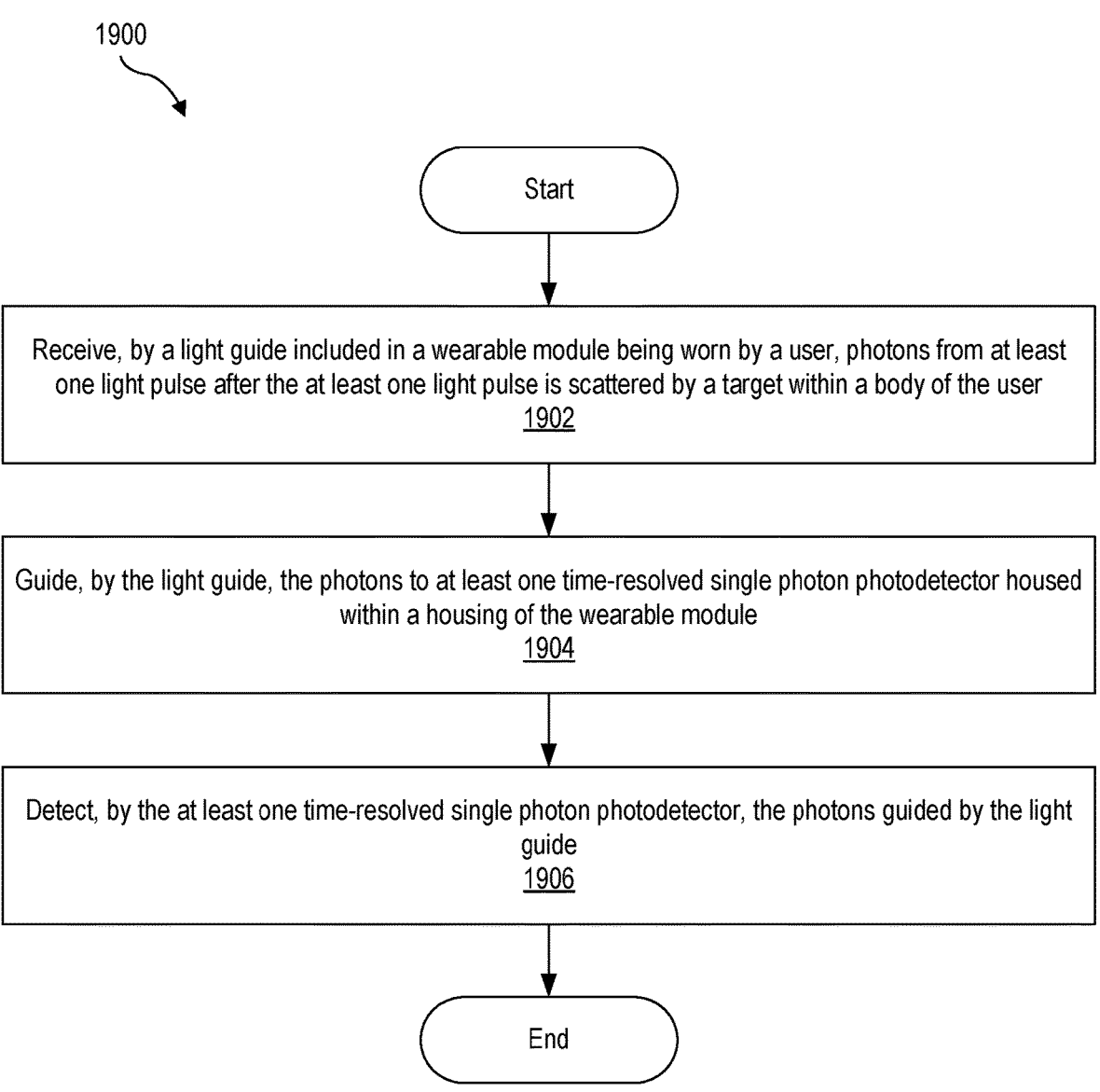

Start

Receive, by a light guide included in a wearable module being worn by a user, photons from at least one light pulse after the at least one light pulse is scattered by a target within a body of the user
1902

Guide, by the light guide, the photons to at least one time-resolved single photon photodetector housed within a housing of the wearable module
1904

Detect, by the at least one time-resolved single photon photodetector, the photons guided by the light guide
1906

End

DETECTOR ASSEMBLIES FOR A WEARABLE MODULE OF AN OPTICAL MEASUREMENT SYSTEM AND INCLUDING SPRING-LOADED LIGHT-RECEIVING MEMBERS

RELATED APPLICATIONS

The present is a continuation of U.S. patent application Ser. No. 17/176,487, filed Feb. 16, 2021, which application claims priority under 35 U.S.C. § 119(e) to U.S. Provisional Patent Application No. 63/038,468, filed Jun. 12, 2020, and to U.S. Provisional Patent Application No. 62/992,559, filed Mar. 20, 2020, and to U.S. Provisional Patent Application No. 62/979,866, filed Feb. 21, 2020. These applications are incorporated herein by reference in their respective entireties.

BACKGROUND INFORMATION

Detecting neural activity in the brain (or any other turbid medium) is useful for medical diagnostics, imaging, neuro-engineering, brain-computer interfacing, and a variety of other diagnostic and consumer-related applications. For example, it may be desirable to detect neural activity in the brain of a user to determine if a particular region of the brain has been impacted by reduced blood irrigation, a hemorrhage, or any other type of damage. As another example, it may be desirable to detect neural activity in the brain of a user and computationally decode the detected neural activity into commands that can be used to control various types of consumer electronics (e.g., by controlling a cursor on a computer screen, changing channels on a television, turning lights on, etc.).

Neural activity and other attributes of the brain may be determined or inferred by measuring responses of tissue within the brain to light pulses. One technique to measure such responses is time-correlated single-photon counting (TCSPC). Time-correlated single-photon counting detects single photons and measures a time of arrival of the photons with respect to a reference signal (e.g., a light source). By repeating the light pulses, TCSPC may accumulate a sufficient number of photon events to statistically determine a histogram representing the distribution of detected photons. Based on the histogram of photon distribution, the response of tissue to light pulses may be determined in order to study the detected neural activity and/or other attributes of the brain.

A photodetector capable of detecting a single photon (i.e., a single particle of optical energy) is an example of a non-invasive detector that can be used in an optical measurement system to detect neural activity within the brain. An exemplary photodetector is implemented by a semiconductor-based single-photon avalanche diode (SPAD), which is capable of capturing individual photons with very high time-of-arrival resolution (a few tens of picoseconds).

BRIEF DESCRIPTION OF THE DRAWINGS

The accompanying drawings illustrate various embodiments and are a part of the specification. The illustrated embodiments are merely examples and do not limit the scope of the disclosure. Throughout the drawings, identical or similar reference numbers designate identical or similar elements.

FIG. 3 illustrates an exemplary timing diagram for performing an optical measurement operation using an optical measurement system.

FIGS. 8 and 9 illustrate cross-sectional views of the wearable module of FIGS. 6A-7B, including an exemplary light source assembly included in the wearable module, taken along the dash-dot-dash line labeled XIII-XIII in FIG. 7A.

FIGS. 18 and 19 illustrate exemplary methods.

DETAILED DESCRIPTION

Optical measurement systems and methods, and wearable modules for use in an optical measurement system, are described herein. For example, an optical measurement system may include a housing including a top surface, a light guide including a distal end portion adapted to protrude from the top surface of the housing, and a spring member configured to bias the distal end portion of the light guide away from the top surface of the housing. The housing is configured to support and/or house other components of the wearable module The light guide is configured to receive, at the distal end portion, photons from a light pulse scattered by a target within a body of a user of the wearable module and guide the received photons toward a photodetector.

The systems and apparatuses described herein provide various benefits and advantages compared with conventional optical measurement systems and apparatuses. For example, the rigid or semi-rigid light guide easily penetrates through a user's hair to physically contact the user's body (e.g., skin). Additionally, the spring member biases the light guide toward the user's body, thereby maintaining the light guide in physical contact with the user's body in spite of movement by the user or other forces acting on the wearable module. Moreover, when the wearable module includes a plurality of light-receiving light guides, the adjustability of the light guides enables them to conform to the topography of the body surface, thereby ensuring that all light guides remain in physical contact with the body surface when the wearable module is worn by the user. Furthermore, maintaining contact of the light guides with the body surface prevents the detection of ambient light, which could otherwise corrupt the detected signal.

Additionally, the adjustable configuration of the light guides can improve comfort to the user as compared with convention configurations. In conventional configurations of optical measurement systems, pressure mismatch across the distal ends of a conventional module can occur due to rigid fibers in a planar arrangement being engaged into a conformal, non-planar tissue geometry. This can lead to discomfort and damage to the tissue uniquely or over time if too much force is applied by the fibers. The systems and apparatuses described herein overcome these problems by providing a wearable module that is adjustable and conformal to non-planar tissue geometry. These and other advantages and benefits of the present systems and apparatuses are described more fully herein and/or will be made apparent in the description herein.

Figure 1:
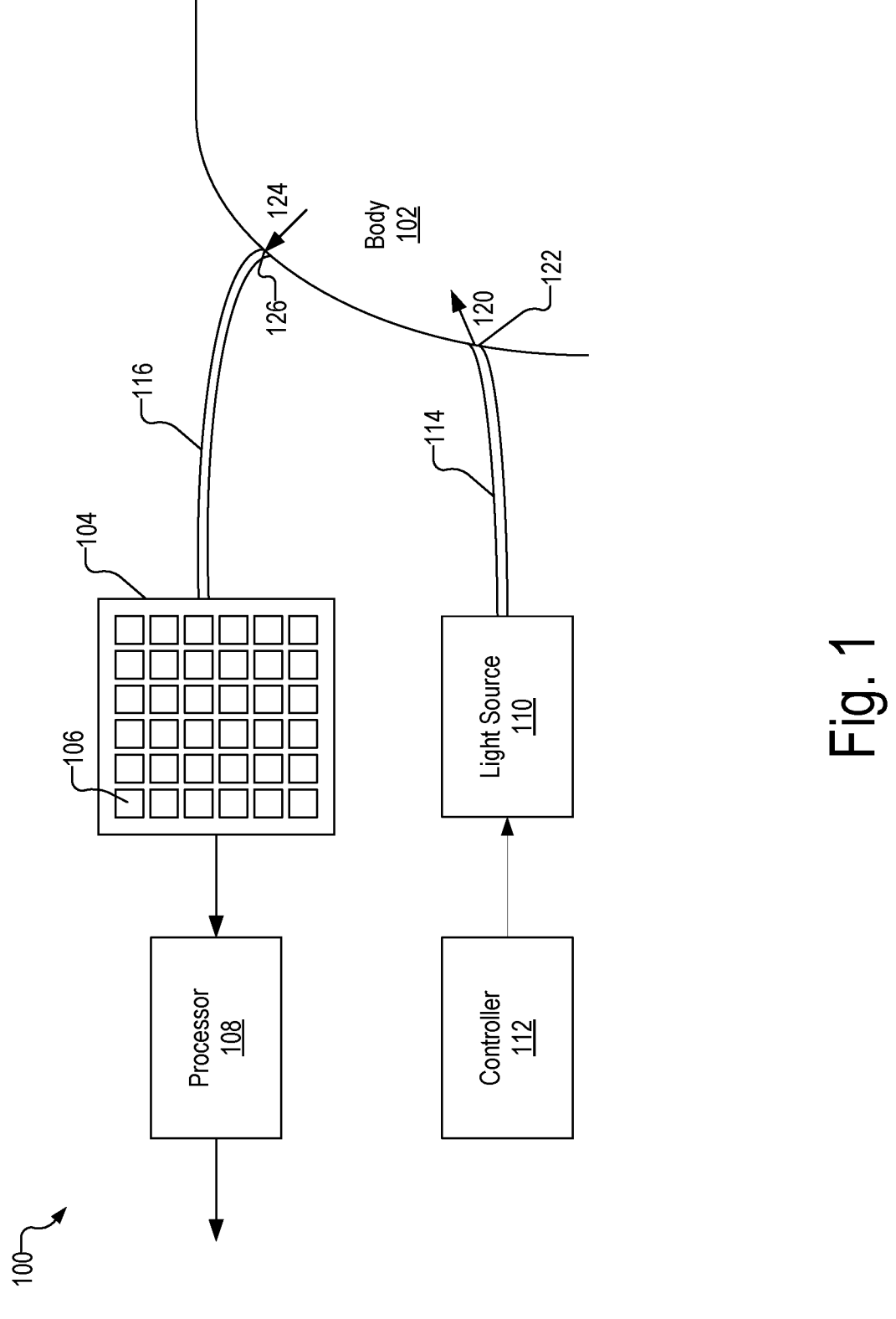
FIG. 1 illustrates an exemplary optical measurement system.

FIG. 1 shows an exemplary optical measurement system 100 configured to perform an optical measurement operation with respect to a body 102. Optical measurement system 100 may in some examples, be portable and/or wearable by a user.

In some examples, optical measurement operations performed by optical measurement system 100 are associated with a time domain-based optical measurement technique. Example time domain-based optical measurement techniques include, but are not limited to, TCSPC, time domain near infrared spectroscopy (TD-NIRS), time domain diffusive correlation spectroscopy (TD-DCS), and time domain digital optical tomography (TD-DOT).

As shown, optical measurement system 100 includes a detector 104 that includes a plurality of individual photodetectors (e.g., photodetector 106), a processor 108 coupled to detector 104, a light source 110, a controller 112, and optical conduits 114 and 116 (e.g., light guides, as described more fully herein). However, one or more of these components may not, in certain embodiments, be considered to be a part of optical measurement system 100. For example, in implementations where optical measurement system 100 is wearable by a user, processor 108 and/or controller 112 may in some embodiments be separate from optical measurement system 100 and not configured to be worn by the user.

Detector 104 may include any number of photodetectors 106 as may serve a particular implementation, such as 2ⁿ photodetectors (e.g., 256, 512, . . . , 16384, etc.), where n is an integer greater than or equal to one (e.g., 4, 5, 8, 10, 11, 14, etc.). Photodetectors 106 may be arranged in any suitable manner.

Photodetectors 106 may each be implemented by any suitable circuit configured to detect individual photons of light incident upon photodetectors 106. For example, each photodetector 106 may be implemented by a single photon avalanche diode (SPAD) circuit and/or other circuitry as may serve a particular implementation.

Processor 108 may be implemented by one or more physical processing (e.g., computing) devices. In some examples, processor 108 may execute instructions (e.g., software) configured to perform one or more of the operations described herein.

Light source 110 may be implemented by any suitable component configured to generate and emit light. For example, light source 110 may be implemented by one or more laser diodes configured to emit light in one or more discrete wavelengths or narrow wavelength bands. In some examples, the light emitted by light source 110 is high coherence light (e.g., light that has a coherence length of at least 5 centimeters) at a predetermined center wavelength. In some examples, the light emitted by light source 110 is emitted as a plurality of alternating light pulses of different wavelengths.

Light source 110 is controlled by controller 112, which may be implemented by any suitable computing device (e.g., processor 108), integrated circuit, and/or combination of hardware and/or software as may serve a particular implementation. In some examples, controller 112 is configured to control light source 110 by turning light source 110 on and off and/or setting an intensity of light generated by light source 110. Controller 112 may be manually operated by a user, or may be programmed to control light source 110 automatically.

Light emitted by light source 110 travels via an optical conduit 114 (e.g., a light pipe, a light guide, a waveguide, a single-mode optical fiber, and/or or a multi-mode optical fiber) to body 102 of a subject. Body 102 may include any suitable turbid medium. For example, in some implementations, body 102 is a head or any other body part of a human or other animal. Alternatively, body 102 may be a non-living object. For illustrative purposes, it will be assumed in the examples provided herein that body 102 is a human head.

As indicated by arrow 120, light emitted by light source 110 enters body 102 at a first location 122 on body 102. Accordingly, a distal end of optical conduit 114 may be positioned at (e.g., right above, in physical contact with, or physically attached to) first location 122 (e.g., to a scalp of the subject). In some examples, the light may emerge from optical conduit 114 and spread out to a certain spot size on body 102 to fall under a predetermined safety limit. At least a portion of light indicated by arrow 120 may be scattered within body 102.

As used herein, "distal" means nearer, along the optical path of the light emitted by light source 110 or the light received by detector 104, to the target (e.g., within body 102) than to light source 110 or detector 104. Thus, the distal end of optical conduit 114 is nearer to body 102 than to light source 110, and the distal end of optical conduit 116 is nearer to body 102 than to detector 104. Additionally, as used herein, "proximal" means nearer, along the optical path of the light emitted by light source 110 or the light received by detector 104, to light source 110 or detector 104 than to body 102. Thus, the proximal end of optical conduit 114 is nearer to light source 110 than to body 102, and the proximal end of optical conduit 116 is nearer to detector 104 than to body 102.

As shown, the distal end of optical conduit 116 (e.g., a light pipe, a light guide, a waveguide, a single-mode optical fiber, and/or a multi-mode optical fiber) is positioned at (e.g., right above, in physical contact with, or physically attached to) output location 126 on body 102. In this manner, optical conduit 116 may collect at least a portion of the scattered light (indicated as light 124) as it exits body 102 at location 126 and carry light 124 to detector 104. Light 124 may pass through one or more lenses and/or other optical elements (not shown) that direct light 124 onto each of the photodetectors 106 included in detector 104.

Photodetectors 106 may be connected in parallel in detector 104. An output of each of photodetectors 106 may be accumulated to generate an accumulated output of detector 104. Processor 108 may receive the accumulated output and determine, based on the accumulated output, a temporal distribution of photons detected by photodetectors 106. Processor 108 may then generate, based on the temporal distribution, a histogram representing a light pulse response of a target (e.g., tissue, blood flow, etc.) in body 102. Example embodiments of accumulated outputs are described herein.

Figure 2:
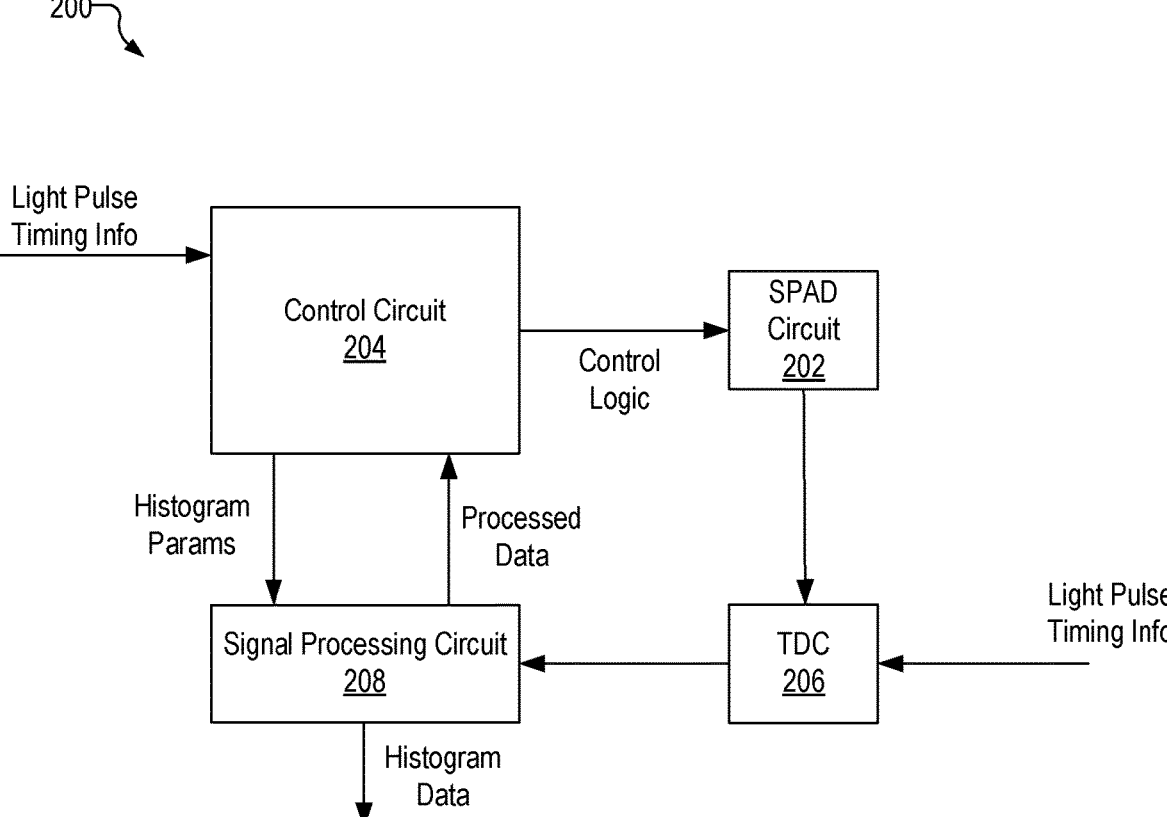
FIG. 2 illustrates an exemplary detector architecture.

FIG. 2 illustrates an exemplary detector architecture 200 that may be used in accordance with the systems and methods described herein. As shown, architecture 200 includes a SPAD circuit 202 that implements photodetector 106, a control circuit 204, a time-to-digital converter (TDC) 206, and a signal processing circuit 208. Architecture 200 may include additional or alternative components as may serve a particular implementation.

In some examples, SPAD circuit 202 includes a SPAD and a fast gating circuit configured to operate together to detect a photon incident upon the SPAD. As described herein, SPAD circuit 202 may generate an output when SPAD circuit 202 detects a photon.

The fast gating circuit included in SPAD circuit 202 may be implemented in any suitable manner. For example, the fast gating circuit may include a capacitor that is pre-charged with a bias voltage before a command is provided to arm the SPAD. Gating the SPAD with a capacitor instead of with an active voltage source, such as is done in some conventional SPAD architectures, has a number of advantages and benefits. For example, a SPAD that is gated with a capacitor may be armed practically instantaneously compared to a SPAD that is gated with an active voltage source. This is because the capacitor is already charged with the bias voltage when a command is provided to arm the SPAD. This is described more fully in U.S. Pat. Nos. 10,158,038 and 10,424,683, which are incorporated herein by reference in their entireties.

In some alternative configurations, SPAD circuit 202 does not include a fast gating circuit. In these configurations, the SPAD included in SPAD circuit 202 may be gated in any suitable manner.

Control circuit 204 may be implemented by an application specific integrated circuit (ASIC) or any other suitable circuit configured to control an operation of various components within SPAD circuit 202. For example, control circuit 204 may output control logic that puts the SPAD included in SPAD circuit 202 in either an armed or a disarmed state.

In some examples, control circuit 204 may control a gate delay, which specifies a predetermined amount of time control circuit 204 is to wait after an occurrence of a light pulse (e.g., a laser pulse) to put the SPAD in the armed state. To this end, control circuit 204 may receive light pulse timing information, which indicates a time at which a light pulse occurs (e.g., a time at which the light pulse is applied to body 102). Control circuit 204 may also control a programmable gate width, which specifies how long the SPAD is kept in the armed state before being disarmed.

Control circuit 204 is further configured to control signal processing circuit 208. For example, control circuit 204 may provide histogram parameters (e.g., time bins, number of light pulses, type of histogram, etc.) to signal processing circuit 208. Signal processing circuit 208 may generate histogram data in accordance with the histogram parameters. In some examples, control circuit 204 is at least partially implemented by controller 112.

TDC 206 is configured to measure a time difference between an occurrence of an output pulse generated by SPAD circuit 202 and an occurrence of a light pulse. To this end, TDC 206 may also receive the same light pulse timing information that control circuit 204 receives. TDC 206 may be implemented by any suitable circuitry as may serve a particular implementation.

Signal processing circuit 208 is configured to perform one or more signal processing operations on data output by TDC 206. For example, signal processing circuit 208 may generate histogram data based on the data output by TDC 206 and in accordance with histogram parameters provided by control circuit 204. To illustrate, signal processing circuit 208 may generate, store, transmit, compress, analyze, decode, and/or otherwise process histograms based on the data output by TDC 206. In some examples, signal processing circuit 208 may provide processed data to control circuit 204, which may use the processed data in any suitable manner. In some examples, signal processing circuit 208 is at least partially implemented by processor 108.

In some examples, each photodetector 106 (e.g., SPAD circuit 202) may have a dedicated TDC 206 associated therewith. For example, for an array of N photodetectors 106, there may be a corresponding array of N TDCs 206. Alternatively, a single TDC 206 may be associated with multiple photodetectors 106. Likewise, a single control circuit 204 and a single signal processing circuit 208 may be provided for one or more SPAD circuits 202 and/or TDCs 206.

FIG. 3 illustrates an exemplary timing diagram 300 for performing an optical measurement operation using optical measurement system 100. The optical measurement operation may be performed in accordance with a time domain-based technique, such as TD-NIRS. Optical measurement system 100 may be configured to perform the optical measurement operation by directing light pulses (e.g., laser pulses) toward a target within a body (e.g., body 102). The light pulses may be short (e.g., 10-2000 picoseconds (ps)) and repeated at a high frequency (e.g., between 100,000 hertz (Hz) and 100 megahertz (MHz)). The light pulses may be scattered by the target and at least a portion of the scattered light may be detected by optical measurement system 100. Optical measurement system 100 may measure a time relative to the light pulse for each detected photon. By counting the number of photons detected at each time relative to each light pulse repeated over a plurality of light pulses, optical measurement system 100 may generate a histogram that represents a light pulse response of the target (e.g., a temporal point spread function (TPSF)). The terms histogram and TPSF are used interchangeably herein to refer to a light pulse response of a target.

Timing diagram 300 shows a sequence of light pulses 302 (e.g., light pulses 302-1 and 302-2) that may be applied to the target (e.g., tissue within a brain of a user, blood flow, a fluorescent material used as a probe in a body of a user, etc.). Timing diagram 300 also shows a pulse wave 304 representing predetermined gated time windows (also referred as gated time periods) during which photodetectors 106 are gated ON to detect photons. As shown, light pulse 302-1 is applied at a time $t_0$. At a time $t_1$, a first instance of the predetermined gated time window begins. Photodetectors 106 may be armed at time $t_1$, enabling photodetectors 106 to detect photons scattered by the target during the predetermined gated time window. In this example, time $t_1$ is set to be at a certain time after time $t_0$, which may minimize photons detected directly from the laser pulse, before the laser pulse reaches the target. However, in some alternative examples, time $t_1$ is set to be equal to time $t_0$.

At a time $t_2$, the predetermined gated time window ends. In some examples, photodetectors 106 may be disarmed at time $t_2$. In other examples, photodetectors 106 may be reset (e.g., disarmed and re-armed) at time $t_2$ or at a time subsequent to time $t_2$. During the predetermined gated time window, photodetectors 106 may detect photons scattered by the target. Photodetectors 106 may be configured to remain armed during the predetermined gated time window such that photodetectors 106 maintain an output upon detecting a photon during the predetermined gated time window. For example, a photodetector 106 may detect a photon at a time $t_3$, which is during the predetermined gated time window between times $t_1$ and $t_2$. The photodetector 106 may be configured to provide an output indicating that the photodetector 106 has detected a photon. The photodetector 106 may be configured to continue providing the output until time $t_2$, when the photodetector may be disarmed and/or reset. Optical measurement system 100 may generate an accumulated output from the plurality of photodetectors. Optical measurement system 100 may sample the accumulated output to determine times at which photons are detected by photodetectors 106 to generate a TPSF.

Figure 4:
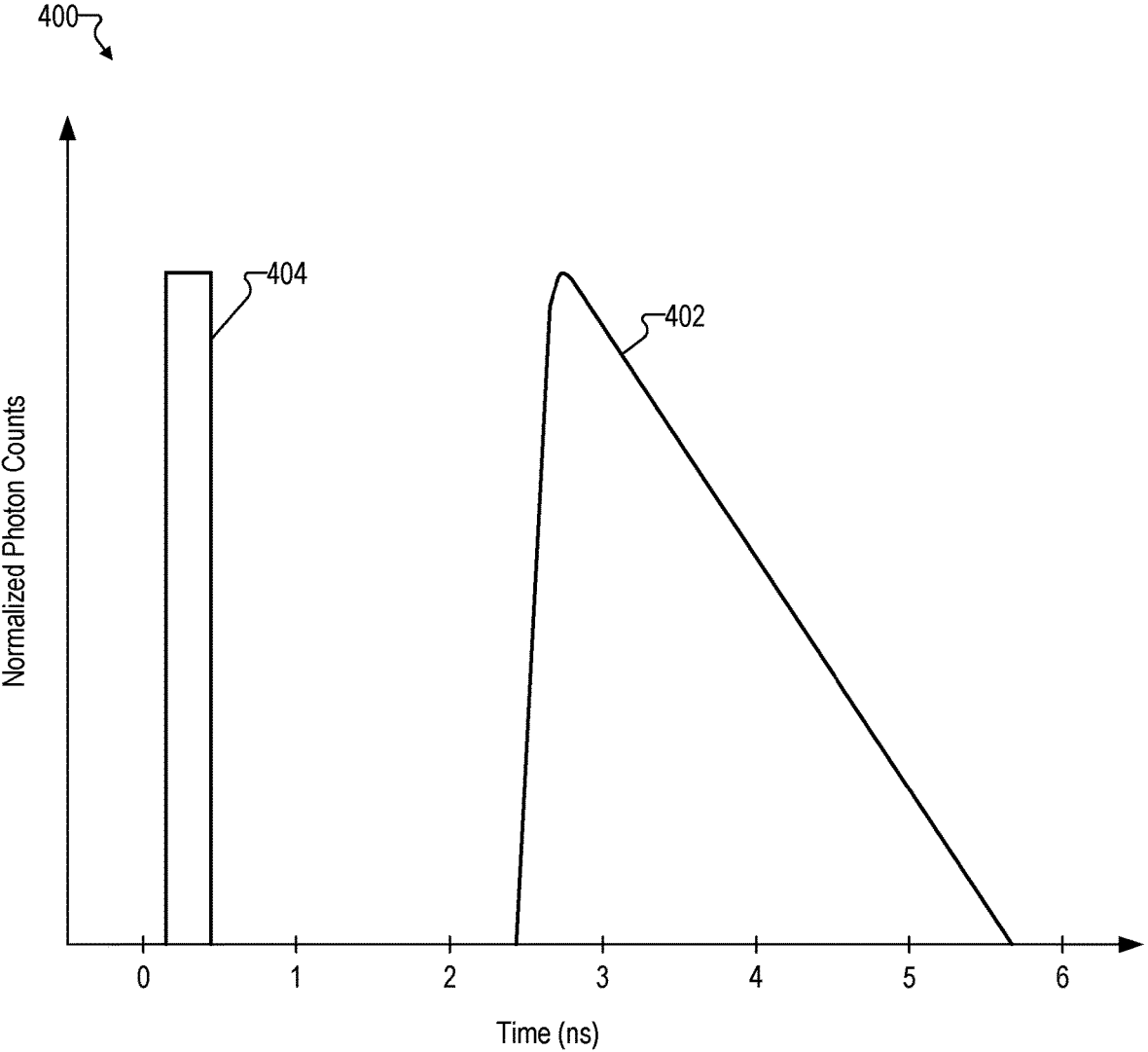
FIG. 4 illustrates a graph of an exemplary temporal point spread function that may be generated by an optical measurement system in response to a light pulse.

FIG. 4 illustrates a graph 400 of an exemplary TPSF 402 that may be generated by optical measurement system 100 in response to a light pulse 404 (which, in practice, represents a plurality of light pulses). Graph 400 shows a normalized count of photons on a y-axis and time bins on an x-axis. As shown, TPSF 402 is delayed with respect to a temporal occurrence of light pulse 404. In some examples, the number of photons detected in each time bin subsequent to each occurrence of light pulse 404 may be aggregated (e.g., integrated) to generate TPSF 402. TPSF 402 may be analyzed and/or processed in any suitable manner to determine or infer biological (e.g., neural) activity.

Optical measurement system 100 may be implemented by or included in any suitable device(s). For example, optical measurement system 100 may be included in a non-wearable device (e.g., a medical device and/or consumer device that is placed near the head or other body part of a user to perform one or more diagnostic, imaging, and/or consumer-related operations). Optical measurement system 100 may alternatively be included, in whole or in part, in a subassembly enclosure of a wearable invasive device (e.g., an implantable medical device for brain recording and imaging).

Alternatively, optical measurement system 100 may be included, in whole or in part, in a non-invasive wearable device that a user may wear to perform one or more diagnostic, imaging, analytical, and/or consumer-related operations. The non-invasive wearable device may be placed on a user's head or other part of the user to detect neural activity. In some examples, such neural activity may be used to make behavioral and mental state analysis, awareness and predictions for the user.

Mental state described herein refers to the measured neural activity related to physiological brain states and/or mental brain states, e.g., joy, excitement, relaxation, surprise, fear, stress, anxiety, sadness, anger, disgust, contempt, contentment, calmness, focus, attention, approval, creativity, positive or negative reflections/attitude on experiences or the use of objects, etc. Further details on the methods and systems related to a predicted brain state, behavior, preferences, or attitude of the user, and the creation, training, and use of neuromes can be found in U.S. Provisional Patent Application No. 63/047,991, filed Jul. 3, 2020. Exemplary measurement systems and methods using biofeedback for awareness and modulation of mental state are described in more detail in U.S. patent application Ser. No. 16/364,338, filed Mar. 26, 2019, published as US2020/0196932A1. Exemplary measurement systems and methods used for detecting and modulating the mental state of a user using entertainment selections, e.g., music, film/video, are described in more detail in U.S. patent application Ser. No. 16/835,972, filed Mar. 31, 2020, published as US2020/0315510A1. Exemplary measurement systems and methods used for detecting and modulating the mental state of a user using product formulation from, e.g., beverages, food, selective food/drink ingredients, fragrances, and assessment based on product-elicited brain state measurements are described in more detail in U.S. patent application Ser. No. 16/853,614, filed Apr. 20, 2020, published as US2020/0337624A1. Exemplary measurement systems and methods used for detecting and modulating the mental state of a user through awareness of priming effects are described in more detail in U.S. patent application Ser. No. 16/885,596, filed May 28, 2020, published as US2020/0390358A1. These applications and corresponding U.S. publications are incorporated herein by reference in their entirety.

Figure 5:
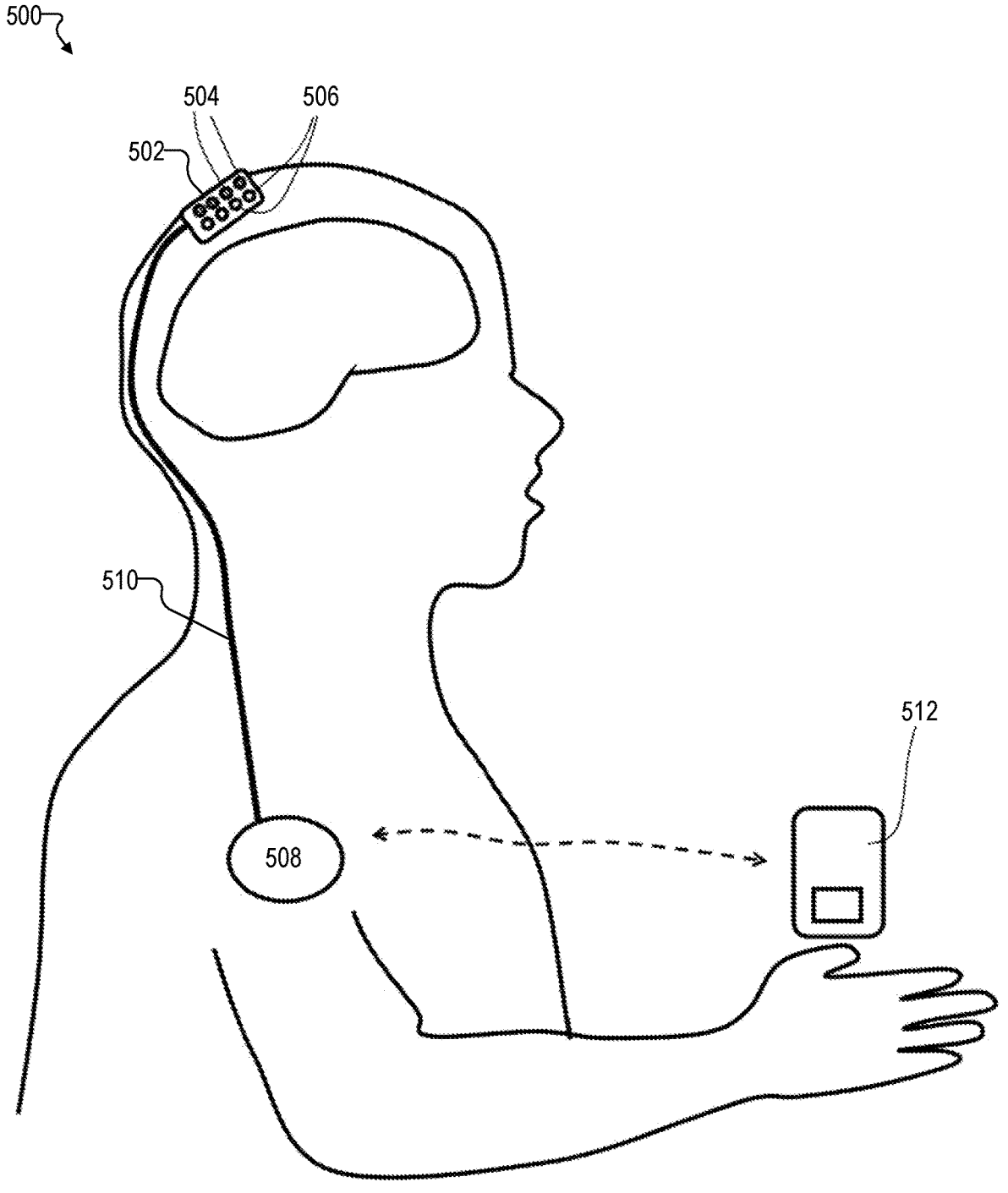
FIG. 5 illustrates an exemplary non-invasive wearable brain interface system.

To illustrate, FIG. 5 shows an exemplary non-invasive wearable brain interface system 500 ("brain interface system 500") that implements optical measurement system 100 (shown in FIG. 1). As shown, brain interface system 500 includes a head-mountable component 502 configured to be attached to and/or worn on a user's head. Head-mountable component 502 may be implemented by a cap shape that is worn on a head of a user. Alternative implementations of head-mountable component 502 include helmets, beanies, headbands, other hat shapes, or other forms conformable to be worn on a user's head, etc. Head-mountable component 502 may be made out of any suitable cloth, soft polymer, plastic, hard shell, and/or any other suitable material as may serve a particular implementation. Examples of headgears used with wearable brain interface systems are described below in more detail and in U.S. Pat. No. 10,340,408, incorporated herein by reference in its entirety.

Head-mountable component 502 includes a plurality of detectors 504, which may implement or be similar to detector 104, and a plurality of light sources 506, which may be implemented by or be similar to light source 110. It will be recognized that in some alternative embodiments, head-mountable component 502 may include a single detector 504 and/or a single light source 506.

Brain interface system 500 may be used for controlling an optical path to the brain and/or for transforming photodetector measurements into an intensity value that represents an optical property of a target within the brain. Brain interface system 500 allows optical detection of deep anatomical locations beyond skin and bone (e.g., skull) by extracting data from photons originating from light sources 506 and emitted to a target location within the user's brain, in contrast to conventional imaging systems and methods (e.g., optical coherence tomography (OCT), continuous wave near infrared spectroscopy (CW-NIRS)), which only image superficial tissue structures or through optically transparent structures.

Brain interface system 500 may further include a processor 508 configured to communicate with (e.g., control and/or receive signals from) detectors 504 and light sources 506 by way of a communication link 510. Communication link 510 may include any suitable wired and/or wireless communication link. Processor 508 may include any suitable housing and may be located on the user's scalp, neck, shoulders, chest, or arm, as may be desirable. In some variations, processor 508 may be integrated in the same assembly housing as detectors 504 and light sources 506. In some examples, processor 508 is implemented by or similar to processor 108 and/or controller 112.

As shown, brain interface system 500 may optionally include a remote processor 512 in communication with processor 508. For example, remote processor 512 may store measured data from detectors 504 and/or processor 508 from previous detection sessions and/or from multiple brain interface systems (not shown). In some examples, remote processor 512 is implemented by or similar to processor 108 and/or controller 112.

Power for detectors 504, light sources 506, and/or processor 508 may be provided via a wearable battery (not shown). In some examples, processor 508 and the battery may be enclosed in a single housing, and wires carrying power signals from processor 508 and the battery may extend to detectors 504 and light sources 506. Alternatively, power may be provided wirelessly (e.g., by induction).

In some alternative embodiments, head mountable component 502 does not include individual light sources. Instead, a light source configured to generate the light that is detected by detector 504 may be included elsewhere in brain interface system 500. For example, a light source may be included in processor 508 and/or in another wearable or non-wearable device and coupled to head mountable component 502 through an optical connection.

Each of the light sources described herein may be implemented by any suitable device. For example, a light source as used herein may be, for example, a distributed feedback (DFB) laser, a super luminescent diode (SLD), a light emitting diode (LED), a diode-pumped solid-state (DPSS) laser, a laser diode (LD), a super luminescent light emitting diode (sLED), a vertical-cavity surface-emitting laser (VC-SEL), a titanium sapphire laser, a micro light emitting diode (mLED), and/or any other suitable laser or light source.

In some alternative embodiments, head mountable component 502 does not include individual detectors 504. Instead, one or more detectors configured to detect the scattered light from the target may be included elsewhere in brain interface system 500. For example, a detector may be included in processor 508 and/or in another wearable or non-wearable device and coupled to head mountable component 502 through an optical connection.

Optical measurement system 100 may be modular in that one or more components of optical measurement system 100 may be removed, changed out, or otherwise modified as may serve a particular implementation. Additionally or alternatively, optical measurement system 100 may be modular such that one or more components of optical measurement system 100 may be housed in a separate housing (e.g., module) and/or may be movable relative to other components. Exemplary modular optical measurement systems are described in more detail in U.S. Provisional Patent Application No. 63/081,754, filed Sep. 22, 2020, U.S. Provisional Patent Application No. 63/038,459, filed Jun. 12, 2020, U.S. Provisional Patent Application No. 63/038,468, filed Jun. 12, 2020, U.S. Provisional Patent Application No. 63/038, 481, filed Jun. 12, 2020, and U.S. Provisional Patent Application No. 63/064,688, filed Aug. 12, 2020, which applications are incorporated herein by reference in their respective entireties.

Figure 6A:
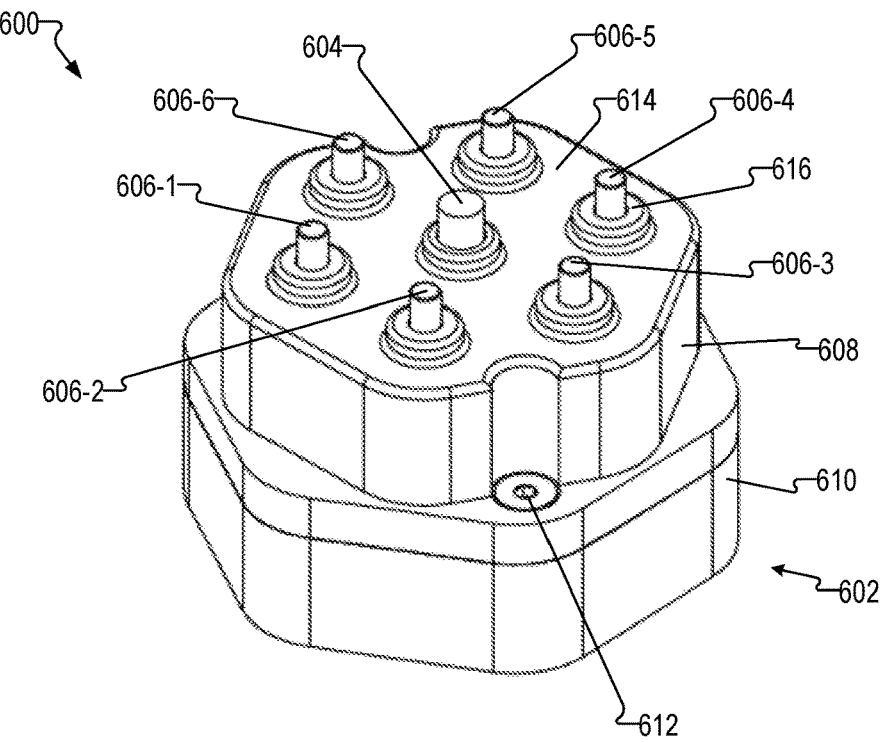
FIGS. 6A, 6B, 7A, and 7B illustrate various views of an exemplary wearable module that may be used in an optical measurement system.
Figure 6B:
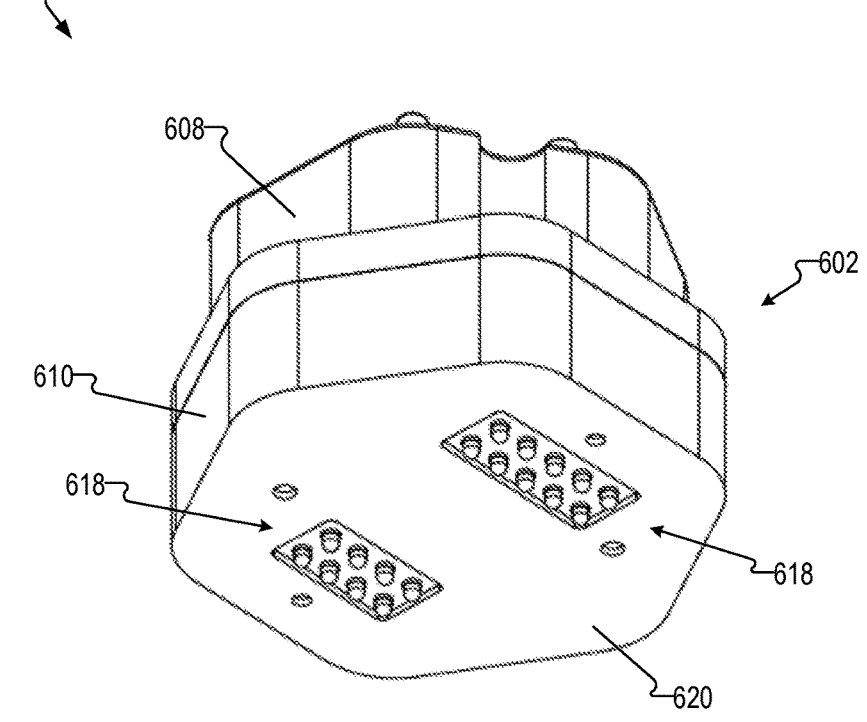
Figure 7A:
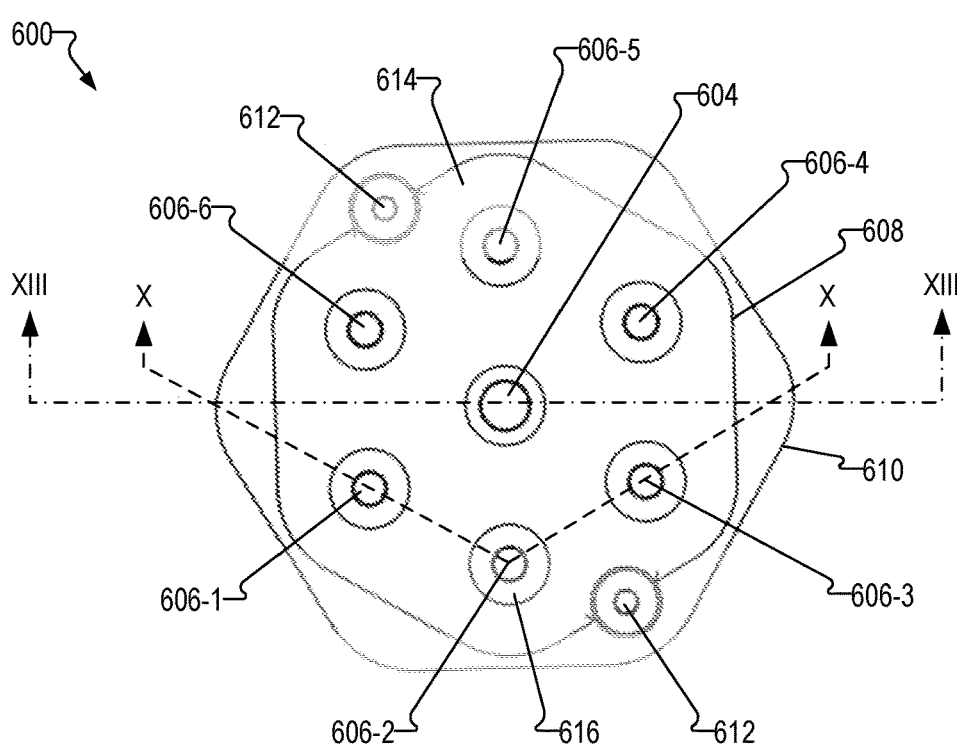
Figure 7B:
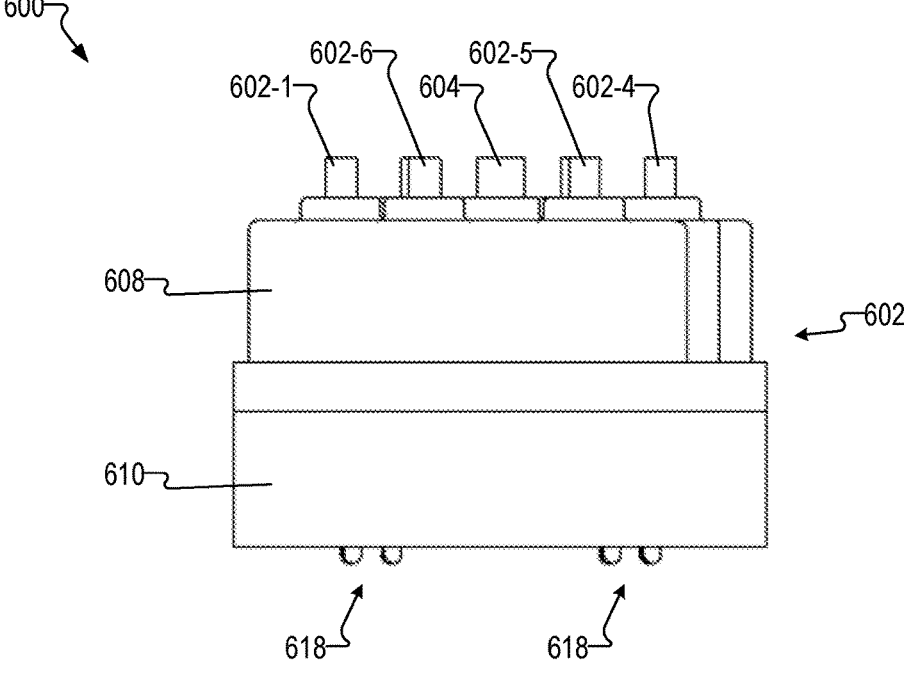

As mentioned, one or more components of optical measurement system 100 (e.g., head-mountable component 502) may be implemented in a wearable module. FIGS. 6A-7B illustrate various views of an exemplary wearable module 600 ("module 600") that may implement one or more components of optical measurement system 100. FIG. 6A shows a perspective view of a top side of module 600, FIG. 6B shows a perspective view of a bottom side of module 600, FIG. 7A shows a plan view of the top side of module 600, and FIG. 7B shows a side view of module 600. In some examples, module 600 may be included in a head-mountable component (e.g., head-mountable component 502) of an optical measurement system (e.g., brain interface system 500).

As shown in FIGS. 6A-7B, module 600 includes a housing 602, a light-emitting member 604, and a plurality of light-receiving members 606 (e.g., light-receiving members 606-1 through 606-6). Module 600 may include any additional or alternative components as may suit a particular implementation.

Housing 602 is configured to support and/or house various components of module 600, including light-emitting member 604 and light-receiving members 606 as well any other components of module 600 not shown in FIGS. 6A-7B (e.g., various components of a light source assembly and/or a plurality of detector assemblies, a controller, a processor, a signal processing circuit, etc.). As shown, housing 602 includes an upper housing 608 and a lower housing 610 joined and held together by fasteners 612 (e.g., screws, bolts, etc.). As used herein with reference to module 600, "upper" refers to a side of module 600 that faces a target within a body of a user when module 600 is worn by the user, and "lower" refers to a side of module 600 that is farthest from the target when module 600 is worn by the user. Light-emitting member 604 and light-receiving members 606 protrude from an upper surface 614 (a target-side surface) of upper housing 608 so that light may be emitted toward and received from the target.

In some examples, as shown in FIGS. 6A, 7A, and 7B, upper housing 608 includes a plurality of frame supports 616 protruding from upper surface 614 and configured to support light-emitting member 604 and light-receiving members 606 in a lateral direction. Frame supports 616 may be formed integrally with upper surface 614 or may be formed separately and attached to upper surface 614.

As shown in FIGS. 6A-7B, upper housing 608 and lower housing 610 have a generally hexagonal shape, and are rotationally offset from one another (e.g., by about 30°). It will be recognized that upper housing 608 and lower housing 610 may alternatively be aligned with one another (rather than rotationally offset), and may alternatively have any other shape as may suit a particular implementation (e.g., rectangular, square, circular, triangular, pentagonal, free-form, etc.). However, a hexagonal shape, along with beveled and/or rounded edges and corners, allows a plurality of modules to be flexibly interconnected adjacent one another in a wearable module assembly (e.g., in a head-mountable component). Thus, a wearable module assembly may conform to three-dimensional surface geometries, such as a user's head. Exemplary wearable module assemblies comprising a plurality of wearable modules are described in more detail in U.S. Provisional Patent Application No. 62/992,550, filed Mar. 20, 2020, which application is incorporated herein by reference in its entirety.

Light-emitting member 604 (e.g., a light-emitting light guide) is configured to emit light (e.g., light indicated by arrow 120, light pulses 302, or light pulse 404) from a distal end (e.g., an upper surface) of light-emitting member 604. Light-emitting member 604 may be implemented by any suitable optical conduit (e.g., optical conduit 114). Light-emitting member 604 is included in a light source assembly that is configured to generate and emit the light toward the target. In the examples shown in FIGS. 6A-7B, the light source assembly is included entirely within module 600. In alternative examples, one or more components of the light source assembly (e.g., light source 110, controller 112, etc.) are located off module 600 and connected (e.g., optically and/or electrically) with components in module 600 (e.g., with light-emitting member 604, etc.). Exemplary light source assemblies that may be included in module 600 will be described below in more detail.

When module 600 is worn by a user, a portion of the light emitted by light-emitting member 604 may be scattered by a target within the body of the user, and a portion of the scattered light (e.g., light 124) may be received by one or more light-receiving members 606 (e.g., one or more light-receiving light guides). Light-receiving members 606 may be implemented by any suitable optical conduit (e.g., optical conduit 116) and/or any other suitable means for conveying light. Light-receiving members 606 are included in a detector assembly configured to receive the scattered light and convey the scattered light (e.g., photons) to a photodetector (e.g., photodetector 106). In the examples shown in FIGS. 6A-7B, the detector assembly is included entirely within module 600. In alternative examples, one or more components of the detector assembly (e.g., detector 104, photodetector 106, processor 108, control circuit 204, TDC 206, signal processing circuit 208, etc.) are located off module 600 and connected (e.g., optically and/or electrically) with components in module 600 (e.g., with light-receiving members 606). Exemplary detector assemblies that may be included in module 600 will be described below in more detail.

As shown in FIG. 6B, module 600 further includes communication interfaces 618 on a lower surface 620 of lower housing 610. Communication interfaces 618 are configured to optically, electrically, and/or communicatively connect module 600 (e.g., components housed within housing 602) with other wearable modules, optical measurement system components (e.g., processor 508, remote processor 512, etc.), and/or any other remote components or devices (e.g., a remote computing device). In some examples, electrical power may be provided to module 600 by way of communication interface 618. Although communication interfaces 618 are shown to be positioned on lower surface 620, communication interfaces 618 may additionally or alternatively be positioned on any other surface of housing 602 as may suit a particular implementation. Additionally or alternatively, module 600 may include any suitable wireless communication interfaces.

Figure 8:
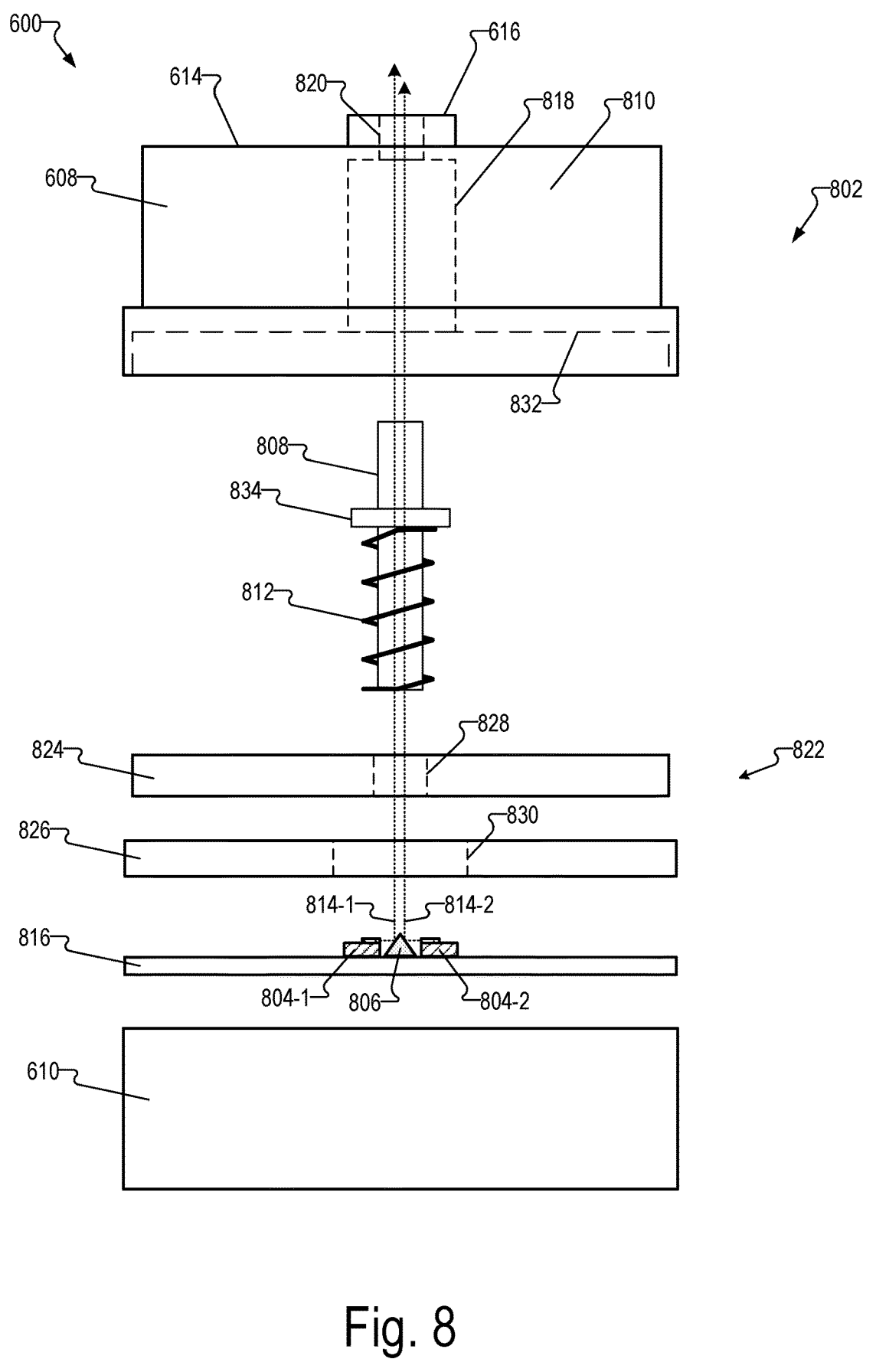
Figure 9:
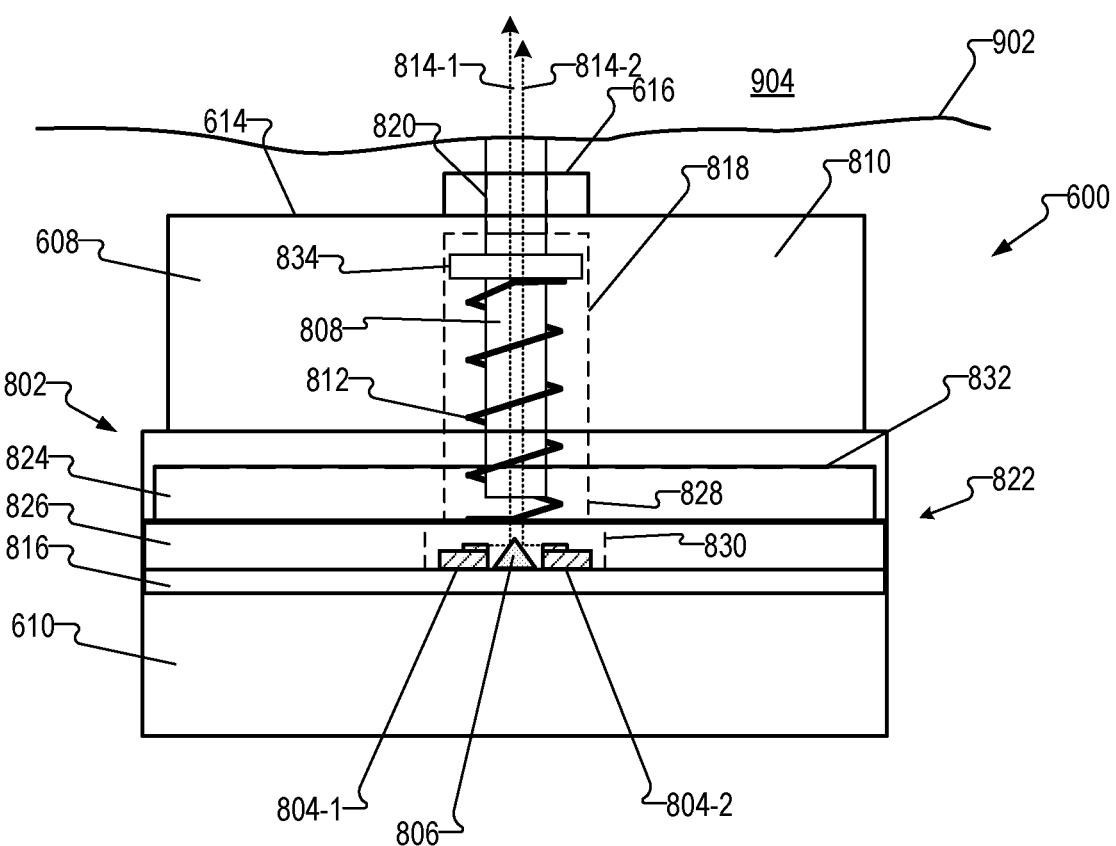

FIGS. 8 and 9 illustrate a cross-sectional view of module 600, including an exemplary light source assembly included in module 600, taken along the dash-dot-dash line labeled XIII-XIII shown in FIG. 7A. FIG. 8 shows an exploded view of module 600, and FIG. 9 shows a view of module 600 in an assembled state as worn by a user. As shown in FIGS. 8 and 9, module 600 includes a light source assembly 802 housed within housing 602. Module 600 may also include any other suitable components that are not shown in FIGS. 8 and 9, such as one or more detector assemblies described below in more detail.

In time domain-based optical measurement systems, such as systems based on TD-NIRS, alternating short light pulses of near-infrared (NIR) light in two or more wavelengths are emitted toward a target. A portion of the emitted light is scattered by the target while a portion of the light is absorbed, such as by hemoglobin (Hb) and deoxygenated hemoglobin (deoxy-Hb). Differences in the absorption spectra of Hb and deoxy-Hb at different wavelengths can be measured and used to determine or infer biological activity (e.g., neural activity).

In conventional configurations of optical measurement systems, a light source capable of emitting light in a plurality of different wavelengths is located away from the user so that the emitted light must be conveyed from the light source to the wearable module by a relatively long optical fiber. This creates various problems. For example, the long optical fibers apply torque and other forces to the wearable module, often causing the wearable module to move and shift around when worn by the user. The movement of the wearable module can degrade the detected signal and the overall performance of the optical measurement system. Additionally, the heavy weight of the fibers can make the wearable module uncomfortable to wear. Furthermore, optical measurement systems using long fibers are large, expensive, and difficult to maintain.

To address these issues, light source assembly 802 included in module 600 includes a plurality of light sources 804 (e.g., a first light source 804-1 and a second light source 804-2), an optical member 806, and a light guide 808. Light source assembly 802 also includes a light guide block 810 and a spring member 812, but light guide block 810 and spring member 812 may be omitted in other embodiments. Moreover, while FIGS. 8 and 9 show two light sources 804 and one optical member 806, light source assembly 802 may include any other suitable number of light sources and/or optical members as may serve a particular implementation.

Each light source 804 is configured to emit light in a distinct wavelength. For example, first light source 804-1 is configured to emit first light 814-1 (e.g., one or more first light pulses) in a first wavelength and second light source 804-2 is configured to emit second light 814-2 (e.g., one or more second light pulses) in a second wavelength that is different from the first wavelength. The first wavelength and the second wavelength may each be a discrete wavelength or narrow wavelength band. For example, the first wavelength may be 750 nm and the second wavelength may be 850 nm. First light source 804-1 and second light source 804-2 may each be implemented by any suitable light source described herein, such as a laser diode configured to emit the first wavelength and the second wavelength, respectively. In some examples, light sources 804 may implement and/or be implemented by light source 110 and/or light source 506. Light sources 804 are disposed (e.g., mounted, attached, etc.) on a light source plate 816, such as but not limited to a printed circuit board ("PCB"). Light source plate 816 may be securely and immovably mounted within housing 602, such as by one or more fasteners (e.g., screws, bolts, snap-fit, etc.).

In the example shown in FIGS. 8 and 9, light sources 804 are configured to emit light 814 in a direction substantially parallel to a top surface of light sources 804 and/or light source plate 816. Accordingly, optical member 806 is disposed on light source plate 816 between light sources 804, and light sources 804 each emit light toward optical member 806. Optical member 806 may be any one or more devices configured to redirect light emitted from light sources 804 toward light guide 808. As shown in FIGS. 8 and 9, optical member 806 is a triangular reflecting prism configured to reflect light 814 at an angle of about 90°.

In alternative embodiments, optical member 806 may be a prism having any other shape (e.g., a 3- or 4-sided pyramid), a mirror, an optical conduit, a diffractive element, a lens, and/or any other suitable optical device that bends or redirects light. In some examples, light source assembly 802 includes a plurality of optical members each configured to redirect light emitted by a particular light source to light guide 808. Additionally or alternatively, light sources 804 may be configured to emit light in any other direction, such as a direction normal to an upper surface of light sources 804 and/or normal to light source plate 816. Accordingly, optical member 806 may be at any other location to receive the emitted light, such as above light sources 804.

Light guide 808 is configured to receive light 814 from optical member 806 and emit light 814 toward a target within a body of a user when module 600 is worn by a user. Light guide 808 may be implemented by any suitable optical conduit described herein. In some examples, light guide 808 implements or is implemented by optical conduit 114. As shown in FIGS. 8 and 9, light guide 808 comprises a rigid, elongate waveguide. In alternative examples, light guide 808 may comprise a bundle of optical fibers. A proximal end portion of light guide 808 is positioned nearest light sources 804 and optical member 806 and receives light 814 from optical member 806. A distal end portion of light guide 808 is configured to protrude from upper surface 614 of upper housing 608 and emit light 814 toward the target. With this configuration, a plurality of light pulses having a plurality of different wavelengths can be emitted toward the target from the same location.

Light guide 808 may be supported within module 600 in any suitable way. In some examples, as shown in FIGS. 8 and 9, light guide 808 is supported by light guide block 810 and spring member 812. Light guide block 810 may be a thick, solid member having a chamber 818 in which light guide 808 and spring member 812 are positioned. A proximal end of chamber 818 opens to the exterior of module 600 through an opening 820 in upper surface 614 and frame support 616. Light guide 808 is positioned within chamber 818 such that the distal end portion of light guide 808 is configured to protrude from upper surface 614 through opening 820. The distal end portion of light guide 808 protruding through opening 820 forms light-emitting member 604. In some examples, as shown in FIGS. 8 and 9, light guide block 810 is implemented by upper housing 608. In alternative embodiments, light guide block 810 is formed separately from upper housing 608 and is mounted inside upper housing 608.

As shown in FIGS. 8 and 9, a support assembly 822 may be positioned over a distal end portion of light guide block 810 to hold light guide 808 and spring member 812 within chamber 818. Support assembly 822 includes a first plate 824 (e.g., a lens plate of a detector assembly, described below in more detail) and a second plate 826 (e.g., a detector plate of the detector assembly). In some examples, support assembly 822 may also include light source plate 816. First plate 824 and second plate 826 include an opening 828 and an opening 830, respectively, to permit the passage of light 814 and/or accommodate light sources 804 and optical member 806. In some examples, light guide block 810 includes a recess portion 832 in which first plate 824 and/or second plate 826 may be positioned. While support assembly 822 is shown as being separate from first plate 824 and second plate 826, in alternative examples light source plate 816 may be implemented by first plate 824 and/or second plate 826. In additional or alternative examples, support assembly 822 includes only one plate.

In some examples, light guide 808 is configured to move within chamber 818 along an optical axis of light guide 808 (e.g., a longitudinal direction of chamber 818, which is a direction extending from the proximal end of chamber 818 to the distal end of chamber 818). Thus, the extent to which the distal end portion of light guide 808 protrudes from upper surface 614 can be adjusted in order to maintain light guide 808 in physical contact with the user's body.

Spring member 812 is configured to bias the distal end portion of light guide 808 away from upper surface 614. Thus, when module 600 is worn by a user, spring member 812 biases the distal end portion of light guide 808 toward a surface of a body (e.g., skin) of the user, thereby helping to ensure that the distal end portion of light guide 808 is in physical contact with the surface of the body. Spring member 812 may bias the distal end portion of light guide 808 away from upper surface 614 in any suitable way.

In some examples, as shown in FIGS. 8 and 9, spring member 812 comprises a coil spring positioned around an external surface light guide 808. A proximal end of spring member 812 pushes against first plate 824, while the distal end of spring member 812 pushes against a flange portion 834 protruding from a portion of light guide 808. Flange portion 834 may be any suitable structure (e.g., a ring) attached to or protruding from light guide 808. By pressing against flange portion 834, spring member 812 pushes the distal end of light guide 808 away from upper surface 614. In alternative embodiments, spring member 812 may be disposed on an upper side of flange portion 834 and configured to pull flange portion 834 (and hence light guide 808) toward the distal end of chamber 818. While FIGS. 8 and 9 show a coil spring, spring member 812 may be implemented by any other suitable device or mechanism configured to bias the distal end of light guide 808 away from upper surface 614 and toward the user's body.

Flange portion 834 has a width (e.g., diameter) approximately equal to a width (e.g., diameter) of chamber 818 (with sufficient tolerance to enable movement of light guide 808) to maintain a lateral position of light guide 808 within chamber 818. Similarly, opening 820 in upper surface 614 and frame support 616 has a width (e.g., diameter) approximately equal to a width (e.g., diameter) of light guide 808 (with sufficient tolerance to enable movement of light guide 808) to maintain a lateral position of light guide 808 within opening 820. With this configuration, a proximal end of light guide 808 may be maintained in optical alignment with optical member 806. In alternative examples, light source assembly 802 does not include spring member 812 or flange portion 834. For instance, chamber 818 may be approximately the same width (e.g., diameter) as light guide 808 and light guide 808 may be immovably attached to light guide block 810 within chamber 818.

To further maintain light guide 808 in optical alignment with optical member 806, as explained above, light source plate 816 is securely mounted within housing 602, thereby preventing movement of light sources 804 and optical member 806 relative to light guide 808.

In some examples, light source assembly 802 may include a controller (e.g., controller 112, processor 508, etc.) configured to control light sources 804 to output one or more light pulses. The controller may be located in any suitable location. In some examples, the controller may be disposed on light source plate 816, support assembly 822, or any other suitable location within housing 602. Alternatively, the controller may be disposed in another device, housing, or module that is separate from module 600 (e.g., a wearable device, a laptop computer, a smartphone, a tablet computer, etc.) and communicatively coupled with light sources 804 by a wired or wireless communication link.

FIG. 9 shows module 600 as worn by a user. A distal end of light guide 808 is in physical contact with a surface 902 of a body 904 of the user. Surface 902 presses the light guide 1004 toward upper surface 614. Spring member 812 pushes light guide 808 in the opposite direction, thereby maintaining the distal end of light guide 808 in physical contact with surface 902 regardless of the topography and geometry of surface 902, and while one or more light-receiving members protruding from upper surface 614 (e.g., light-receiving members 606) are also in physical contact with surface 902. Light 814 emitted by light sources 804 enters body 904 and is scattered by a target within body 904. At least a portion of the scattered light returns toward module 600 and may be received by one or more light-receiving members 606 included in module 600. Light-receiving members 606 may be included in one or more detector assemblies included in module 600, as will now be described.

In the example shown in FIGS. 8 and 9, module 600 may be included in a time domain-based optical measurement system, such as a system based on TD-NIRS. In conventional configurations of an optical measurement system based on time domain techniques, a user may wear a module that emits light (e.g., NIR) to the user's body and collects the emitted light that has been scattered by tissue in the body. However, in the conventional configurations the detector is located away from the user so that the collected light must be conveyed from the wearable module to the detector by a long optical fiber. This creates several problems. First, when the wearable module is worn on a head of the user it is difficult for the distal end of light-collecting optical fibers to penetrate through the user's hair and maintain physical contact with the user's skin. Second, optical measurement systems that have many detectors require many optical fibers. Third, as explained above, the weight of the optical fibers may cause the module to move and shift around on the user's head, thus causing motion artifacts in the detected signal. Fourth, the length of the optical fibers generates temporal dispersion in the detected signal (e.g., TPSF) because some photons of the collected light are internally reflected many more times within the long optical fibers than other photons due to their different angle-of-incidence on the distal end of the optical fibers. In time domain-based systems, the variation in the time-of-flight of photons affects the TPSF and masks tissue response to the emitted light.

Figure 10:
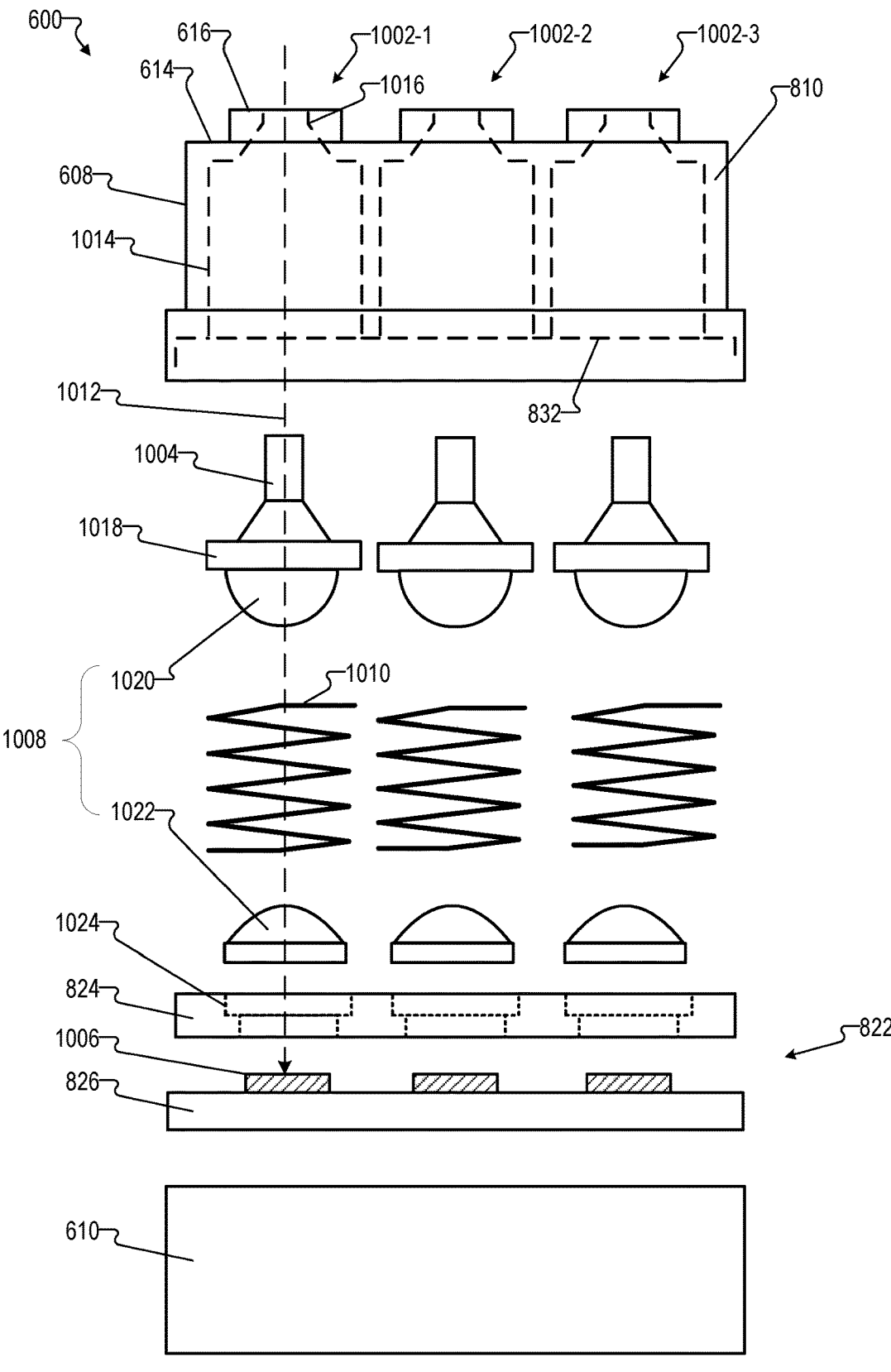
FIGS. 10 and 11 illustrate cross-sectional views of the module of FIGS. 6A-7B, including an exemplary detector assembly included in the wearable module, taken along the dashed line labeled X-X in FIG. 7A.
Figure 11:
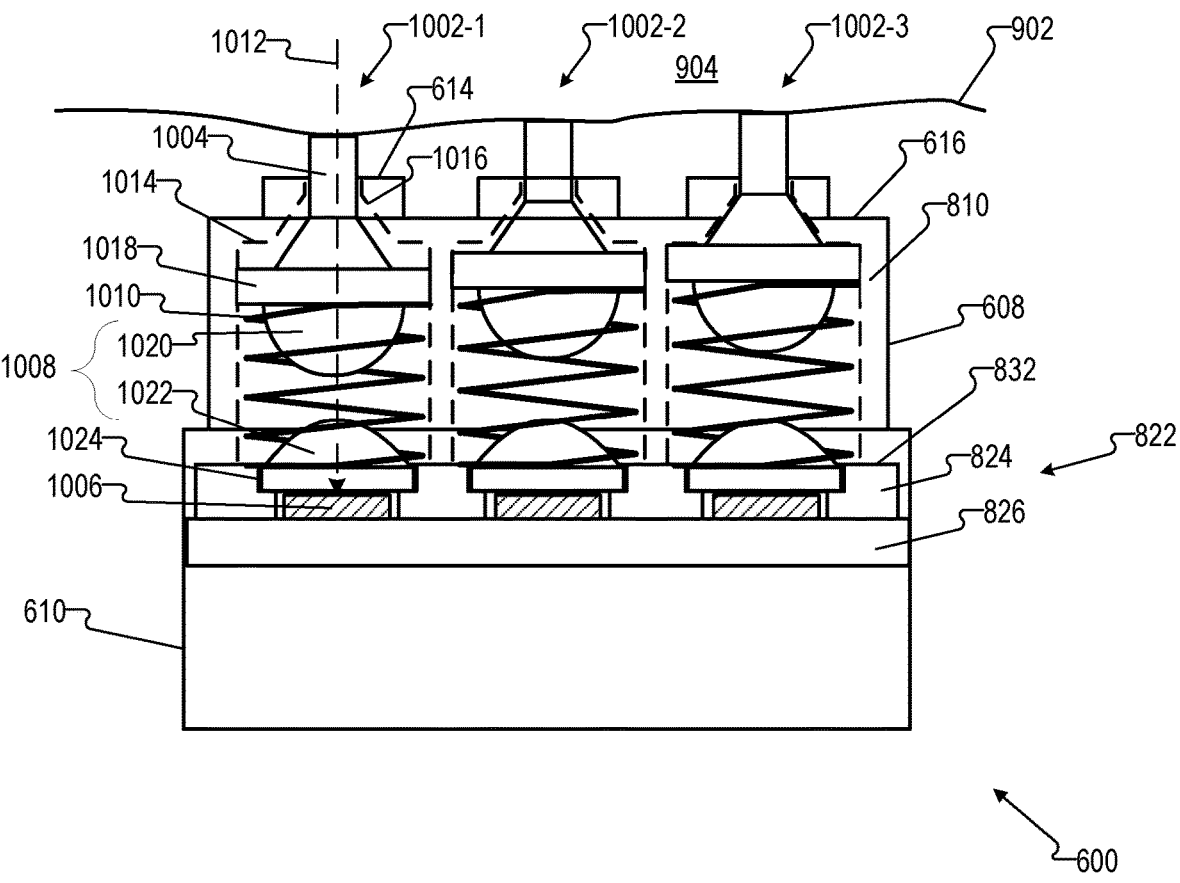

To address these issues, module 600, when used in a time domain-based optical measurement system, may include a plurality of detector assemblies, as will now be explained with reference to FIGS. 10 and 11. FIGS. 10 and 11 show a cross-sectional view of module 600, including exemplary detector assemblies included in module 600, taken along the dashed line labeled X-X shown in FIG. 7A. FIG. 10 shows an exploded view of module 600, and FIG. 11 shows a view of module 600 in an assembled state as worn by a user. As shown in FIGS. 10 and 11, module 600 includes a plurality of detector assemblies housed within housing 602. Module 600 may also include any other suitable components that are not shown in FIGS. 10 and 11, such as light source assembly 802 described above.

Each light-receiving member 606 (see FIGS. 6A-7B) in module 600 may be included in a distinct detector assembly 1002. FIGS. 10 and 11 show exemplary detector assemblies 1002-1, 1002-2, and 1002-3 corresponding to light-receiving members 606-1, 606-2, and 606-3, respectively. Detector assemblies corresponding to light-receiving members 606-4, 606-5, and 606-6 are also included in module 600 but are not shown in the cross-sectional view of FIGS. 10 and 11. Detector assembly 1002-1 will now be described. The following description applies equally to the other detector assemblies 1002 included in module 600.

As shown, detector assembly 1002 includes a light guide 1004 and a detector 1006. Detector assembly 1002 also includes a lens system 1008, light guide block 810, a spring member 1010, and support assembly 822, but one or more of these components may be omitted in other embodiments.

Light guide 1004 is configured to receive light scattered by the target ("light 1012") and guide light 1012 (e.g., photons) toward detector 1006. Light guide 1004 may be implemented by any suitable optical conduit described herein. As shown in FIGS. 10 and 11, light guide 1004 comprises a rigid, elongate waveguide. In alternative examples, light guide 1004 may comprise a bundle of optical fibers. In some examples, light guide 1004 implements optical conduit 116 to receive and guide light 124. A distal end portion of light guide 1004 is configured to protrude from upper surface 614 of upper housing 608 and receive light 1012 from the target. A proximal end portion of light guide 1004 is positioned near detector 1006 and emits light 1012 toward detector 1006.

Light guide 1004 may be supported within module 600 in any suitable way. In some examples, as shown in FIGS. 10 and 11, light guide 1004 is supported by light guide block 810 and spring member 1010. Light guide block 810 has a chamber 1014 in which light guide 1004 and spring member 1010 are positioned. A proximal end of chamber 1014 opens to the exterior of module 600 through an opening 1016 in upper surface 614 and frame support 616. Light guide 1004 is positioned within chamber 1014 such that the distal end portion of light guide 1004 is configured to protrude from upper surface 614 through opening 1016. The distal end portion of light guide 1004 protruding through opening 1016 forms light-receiving member 606-1.

In some examples, light guide 1004 is supported in a light guide block that is separate from light guide block 810. For example, light guide 1004 may be supported in a light guide block formed separately from upper housing 608 but that is mounted inside upper housing 608 and/or within another chamber (not shown) of light guide block 810.

As shown in FIGS. 10 and 11, support assembly 822 (e.g., first plate 824 and/or second plate 826) may be positioned over a distal end portion of light guide block 810 to hold light guide 1004 and spring member 1010 within chamber 1014.

In some examples, light guide 1004 is configured to move within chamber 1014 along an optical axis of light guide 1004 (e.g., a longitudinal direction of chamber 1014, which is a direction extending from the proximal end of chamber 1014 to the distal end of chamber 1014). Thus, the extent to which the distal end portion of light guide 1004 protrudes from upper surface 614 can be adjusted in order to maintain light guide 1004 in physical contact with the user's body.

Spring member 1010 is configured to bias the distal end portion of light guide 1004 away from upper surface 614. Thus, when module 600 is worn by a user, spring member 1010 biases the distal end portion of light guide 1004 toward a surface of the user's body, thereby helping to ensure that the distal end portion of light guide 1004 is in physical contact with the surface of the body. Spring member 1010 may bias the distal end portion of light guide 1004 away from upper surface 614 in any suitable way.

In some examples, as shown in FIGS. 10 and 11, spring member 1010 comprises a coil spring that wraps around an external surface of light guide 1004. A proximal end of spring member 1010 pushes against first plate 824, while the distal end of spring member 1010 pushes against a flange portion 1018 protruding from a portion of light guide 1004. Flange portion 1018 may be any suitable structure (e.g., a ring) attached to or protruding from light guide 1004. In some examples, flange portion 1018 is formed integrally with light guide 1004. By pressing against flange portion 1018, spring member 1010 biases the distal end of light guide 1004 away from upper surface 614. In alternative embodiments, spring member 1010 may be disposed on an upper side of flange portion 1018 and configured to pull flange portion 1018 (and hence light guide 1004) toward the distal end of chamber 1014. While FIGS. 10 and 11 show a coil spring, spring member 1010 may be implemented by any other suitable device or mechanism configured to bias the distal end of light guide 1004 away from upper surface 614 and toward the user's body.

Flange portion 1018 has a width (e.g., diameter) approximately equal to a width (e.g., diameter) of chamber 1014 (with sufficient tolerance to enable movement of light guide 1004) to maintain a lateral position of light guide 1004 within chamber 1014. Similarly, opening 1016 in upper surface 614 and frame support 616 has a width (e.g., diameter) approximately equal to a width (e.g., diameter) of light guide 1004 (with sufficient tolerance to enable movement of light guide 1004) to maintain a lateral position of light guide 1004 within opening 1016. With this configuration, a proximal end of light guide 1004 may be maintained in optical alignment with detector 1006. In alternative examples, detector assembly 1002-1 does not include spring member 1010. For instance, chamber 1014 may be approximately the same width (e.g., diameter) as light guide 1004 and light guide 1004 may be immovably attached to light guide block 810 within chamber 1014.

To further maintain light guide 1004 in optical alignment with detector 1006, detector 1006 is mounted on support assembly 822 (e.g., on first plate 824 or second plate 826), and support assembly 822 is securely and immovably mounted within housing 602, thereby preventing movement of detector 1006 relative to light guide 1004.

To eliminate a lossy interface between light guide 1004 and detector 1006 while allowing light guide 1004 to move relative to detector 1006, detector assembly 1002-1 includes lens system 1008. Lens system 1008 includes a first lens 1020 and a second lens 1022. First lens 1020 is configured to collimate light 1012 within chamber 1014. In some examples, first lens 1020 is formed integrally with light guide 1004 and/or flange portion 1018, and thus moves within chamber 1014 as light guide 1004 moves (due to action of spring member 1010 and/or pushing by the user's body). As shown in FIGS. 10 and 11, first lens 1020 fits inside spring member 1010 and thus directs light through a center opening of spring member 1010 to second lens 1022.

Second lens 1022 is configured to focus light 1012 onto detector 1006. Second lens 1022 is supported on first plate 824. Second lens 1022 may be supported on first plate 824 in any suitable way. As shown, second lens 1022 is positioned within a recess 1024 in first plate 824, thereby maintaining the position of second lens 1022 fixed relative to first lens 1020. In some embodiments, first plate 824 may be transparent (e.g., formed of glass), and second lens 1022 may be affixed to first plate 824 by a transparent adhesive. In yet other embodiments, second lens 1022 is formed integrally with an optically transparent first plate 824. Detector 1006 is mounted on second plate 826 in an optical path of light 1012. Thus, second lens 1022 focuses light 1012 onto detector 1006. With this configuration of lens system 1008, light 1012 at the proximal end of light guide 1004 is imaged onto detector 1006, thereby eliminating a lossy interface between light guide 1004 and detector 1006.

Detector 1006 may be implemented by any suitable detector described herein (e.g., detector 104, photodetector 106, etc.). In embodiments in which module 600 is configured for use in a time domain-based optical measurement system, detector 1006 may include at least one time-resolved single photon photodetector configured to detect photons from at least one light pulse after the at least one light pulse is scattered by the target. In some examples, detector 1006 comprises a plurality of SPAD circuits (e.g., an array of SPAD circuits 202).

In some examples, other circuitry associated with detector 1006 may also be included in module 600 (e.g., housed within housing 602). For instance, any one or more components of detector architecture 200 (e.g., control circuit 204, TDC 206, and/or signal processing circuit 208) may be housed, partially or entirely, within housing 602. These components may for example, be disposed on support assembly 822 (e.g., first plate 824 and/or second plate 826) and/or light source plate 816. Additionally or alternatively, any one or more components of detector architecture 200 may be housed, partially or entirely, within an additional housing of another device that is separate from but communicatively coupled with module 600 (e.g., with detector 1006) by a wired or wireless communication link. The other device may be another wearable device or a non-wearable device.

FIG. 11 shows module 600 as worn by a user. A distal end of each light guide 1004 (e.g., light guide 1004-1 through 1004-3) is in physical contact with surface 902 of body 904 of the user. Surface 902 presses the light guide 1004 toward upper surface 614. Spring member 1010 pushes light guide 1004 in the opposite direction, thereby maintaining the distal end of each light guide 1004 in physical contact with surface 902 regardless of the topography and geometry of surface 902, and regardless of movement by the user, even when light guide 808 is also in physical contact with surface 902. With this configuration, scattered light 1012 from the target is received by light guides 1004 and directed to detector 1006. Moreover, maintaining the distal end of each light guide 1004 in physical contact with surface 902 prevents ambient light from entering light guide 1004 and corrupting the detected signal.

In the configurations just described, light guides 1004 may have a total length of about 10 mm or less, about 5 mm of less, or even 3 mm or less. As a result, the total distance a photon travels from the distal end portion of light guide 1004 to detector 1006 may be approximately 50 mm or less, 40 mm or less, or even 30 mm or less. Such short distances practically eliminates, or renders negligible, any temporal dispersion in the detected signal.

FIGS. 12-17 illustrate embodiments of a wearable device 1200 that includes elements of the optical measurement systems described herein. In particular, the wearable devices 1200 include a plurality of modules 1202, similar to wearable module 600 shown in FIGS. 6A-7B, described herein. For example, each module 1202 includes a source (e.g., light-emitting member 604) and a plurality of detectors (e.g., light-receiving members 606-1 through 606-6). The source may be implemented by one or more light sources similar to light source 110 (shown in FIG. 1). Each detector may implement or be similar to detector 104 (shown in FIG. 1) and may include a plurality of photodetectors. The wearable devices 1200 may each also include a controller (e.g., controller 112) and a processor (e.g., processor 108) and/or be communicatively connected to a controller and processor. In general, wearable device 1200 may be implemented by any suitable headgear and/or clothing article configured to be worn by a user. The headgear and/or clothing article may include batteries, cables, and/or other peripherals for the components of the optical measurement systems described herein. In some examples, the headgear includes one or more modules 600. Additionally or alternatively, modules 1202 are included in or implemented by modules 600.

Figure 12:
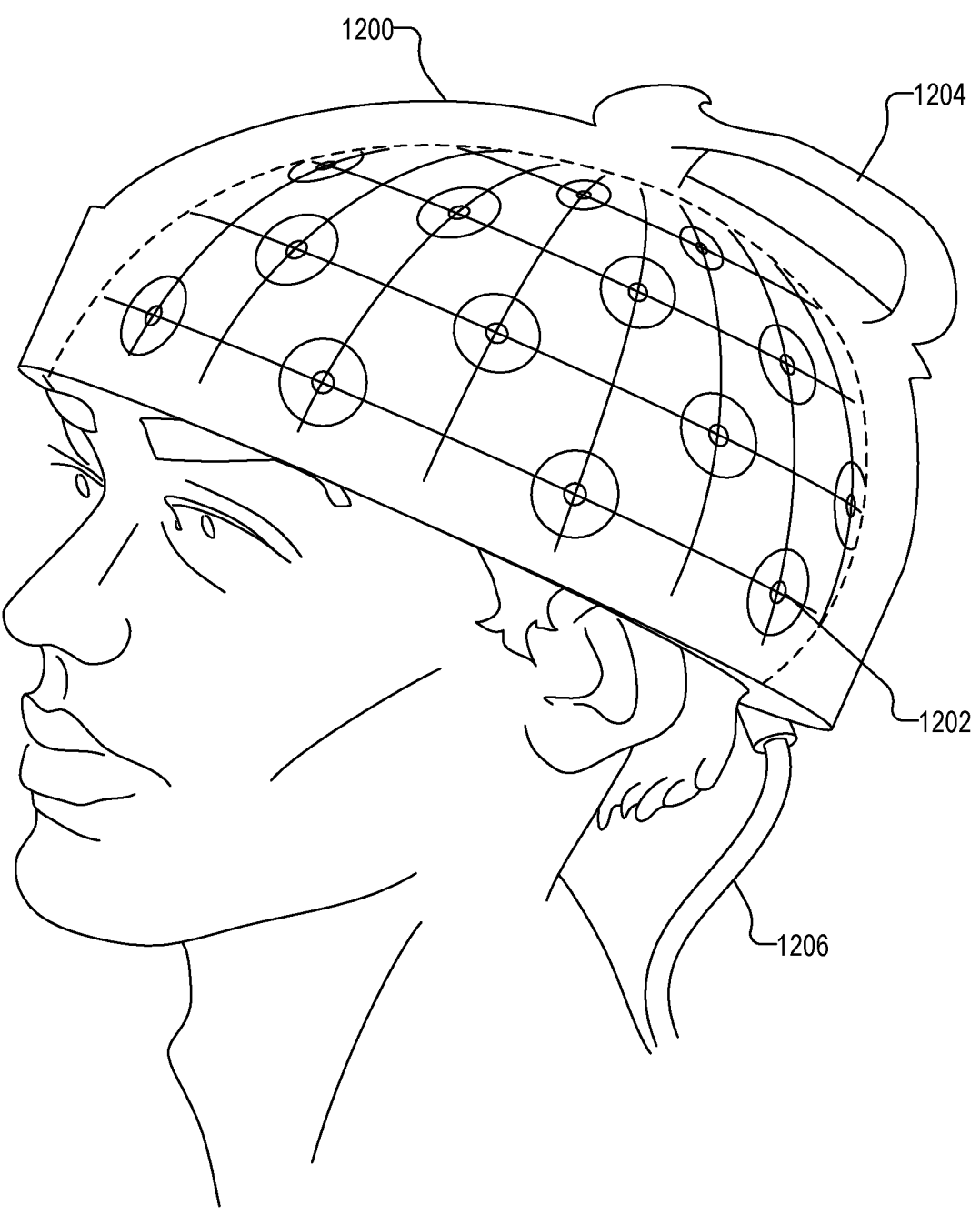
FIGS. 12-17 illustrate embodiments of a wearable device that includes elements of the optical detection systems described herein.
Figure 13:
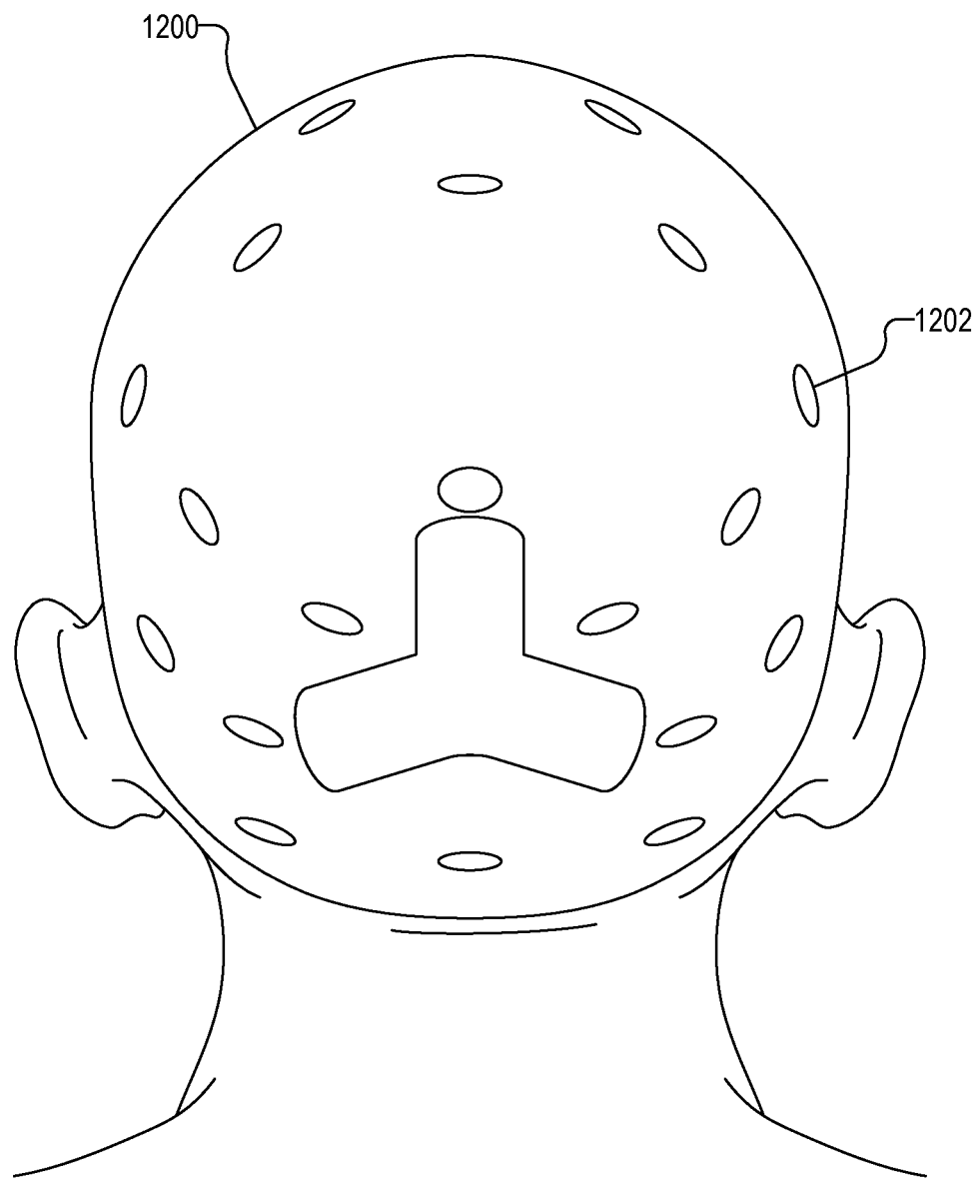
Figure 14:
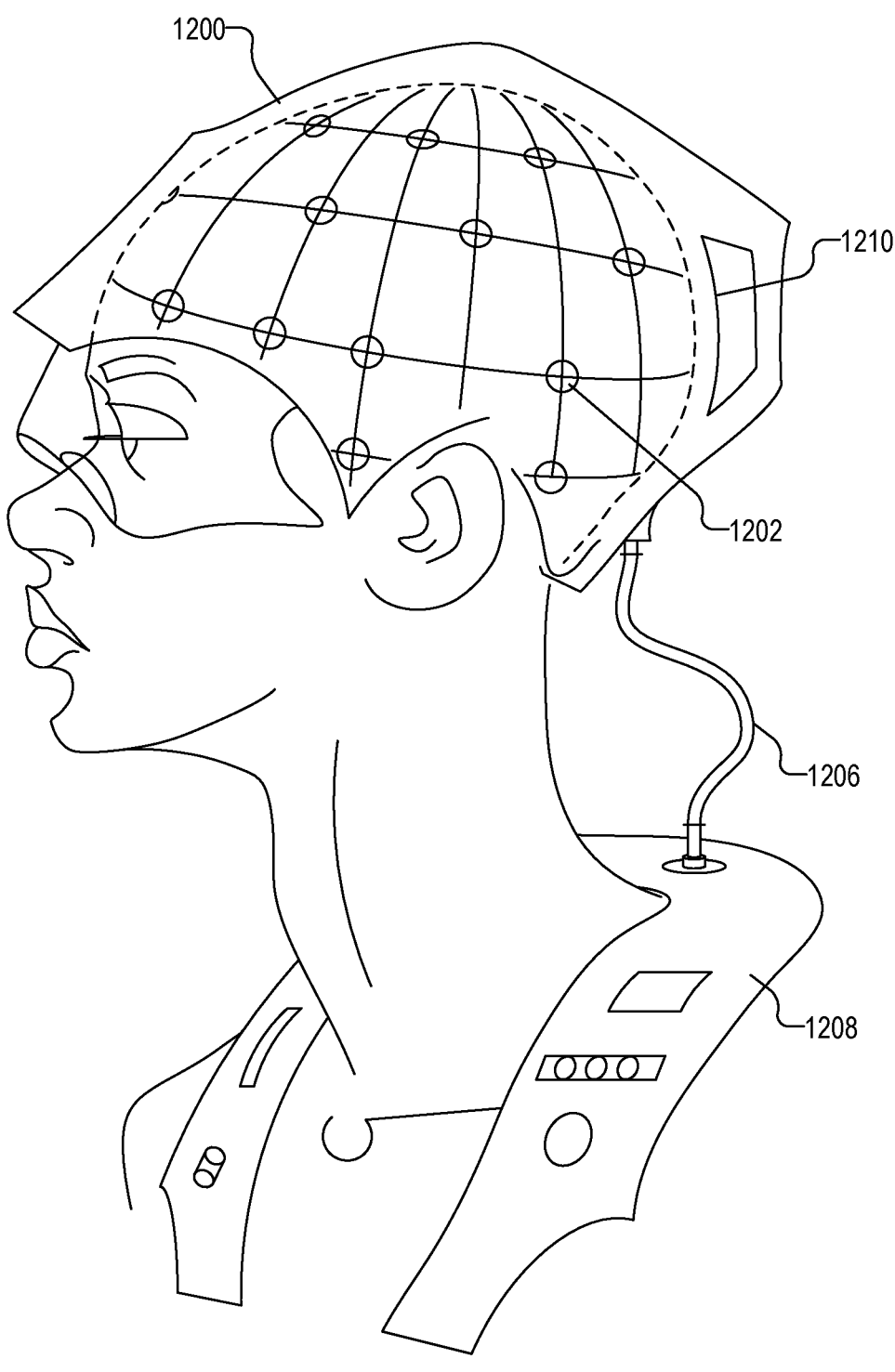

FIG. 12 illustrates an embodiment of a wearable device 1200 in the form of a helmet with a handle 1204. A cable 1206 extends from the wearable device 1200 for attachment to a battery or hub (with components such as a processor or the like). FIG. 13 illustrates another embodiment of a wearable device 1200 in the form of a helmet showing a back view. FIG. 14 illustrates a third embodiment of a wearable device 1200 in the form of a helmet with the cable 1206 leading to a wearable garment 1208 (such as a vest or partial vest) that can include a battery or a hub. Alternatively or additionally, the wearable device 1200 can include a crest 1210 or other protrusion for placement of the hub or battery.

Figure 15:
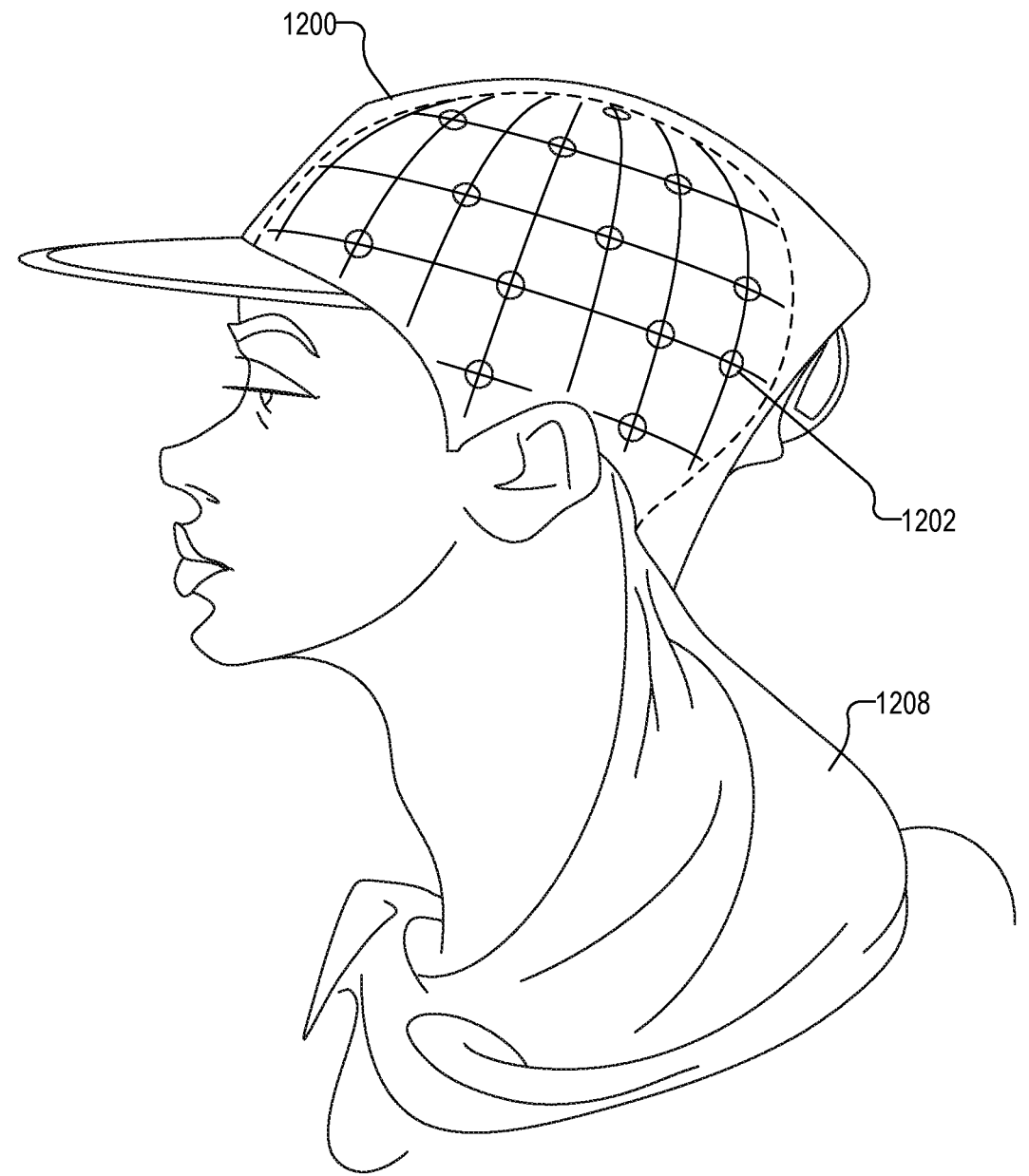

FIG. 15 illustrates another embodiment of a wearable device 1200 in the form of a cap with a wearable garment

19

Figure 16:
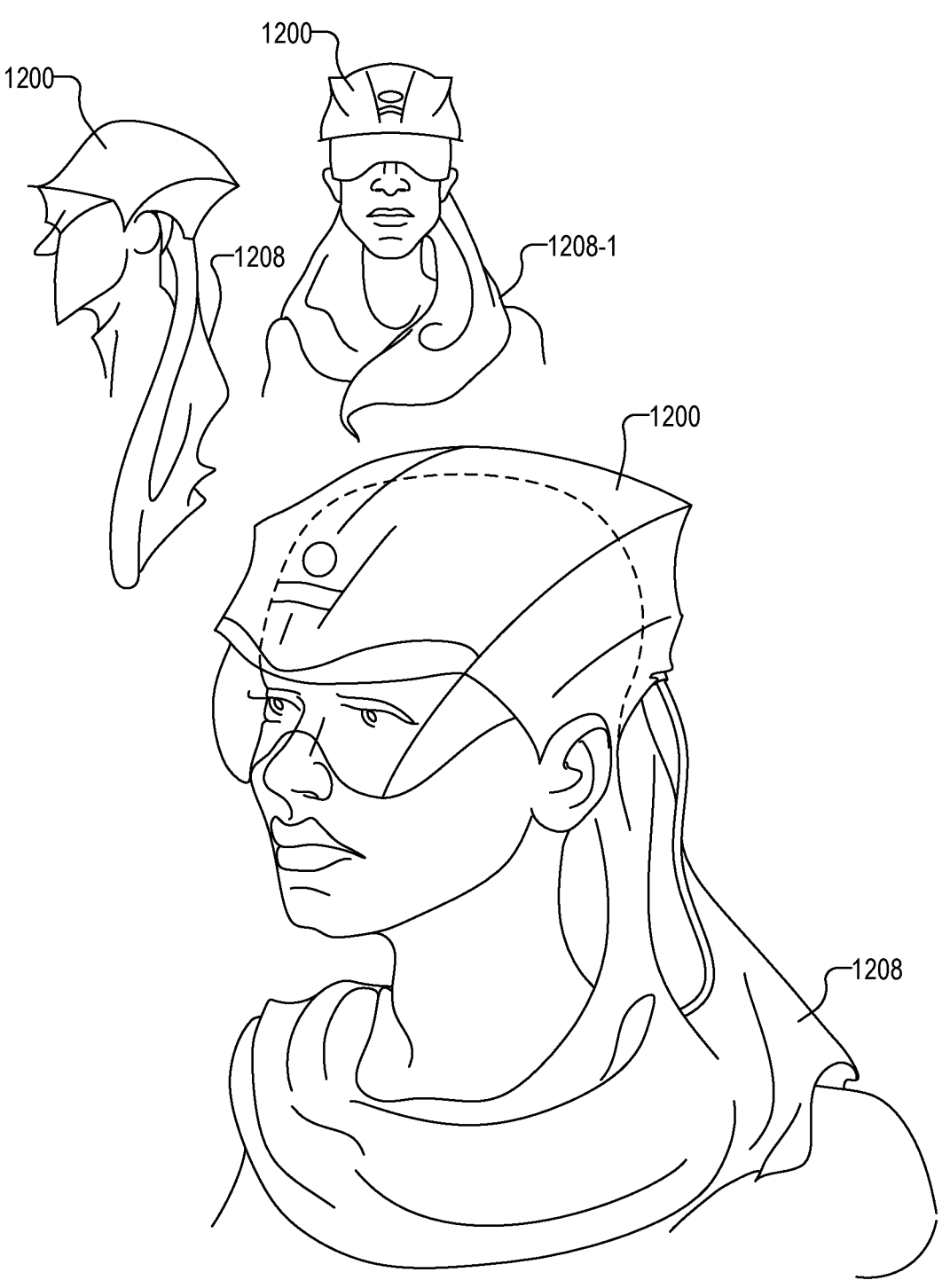
Figure 17:
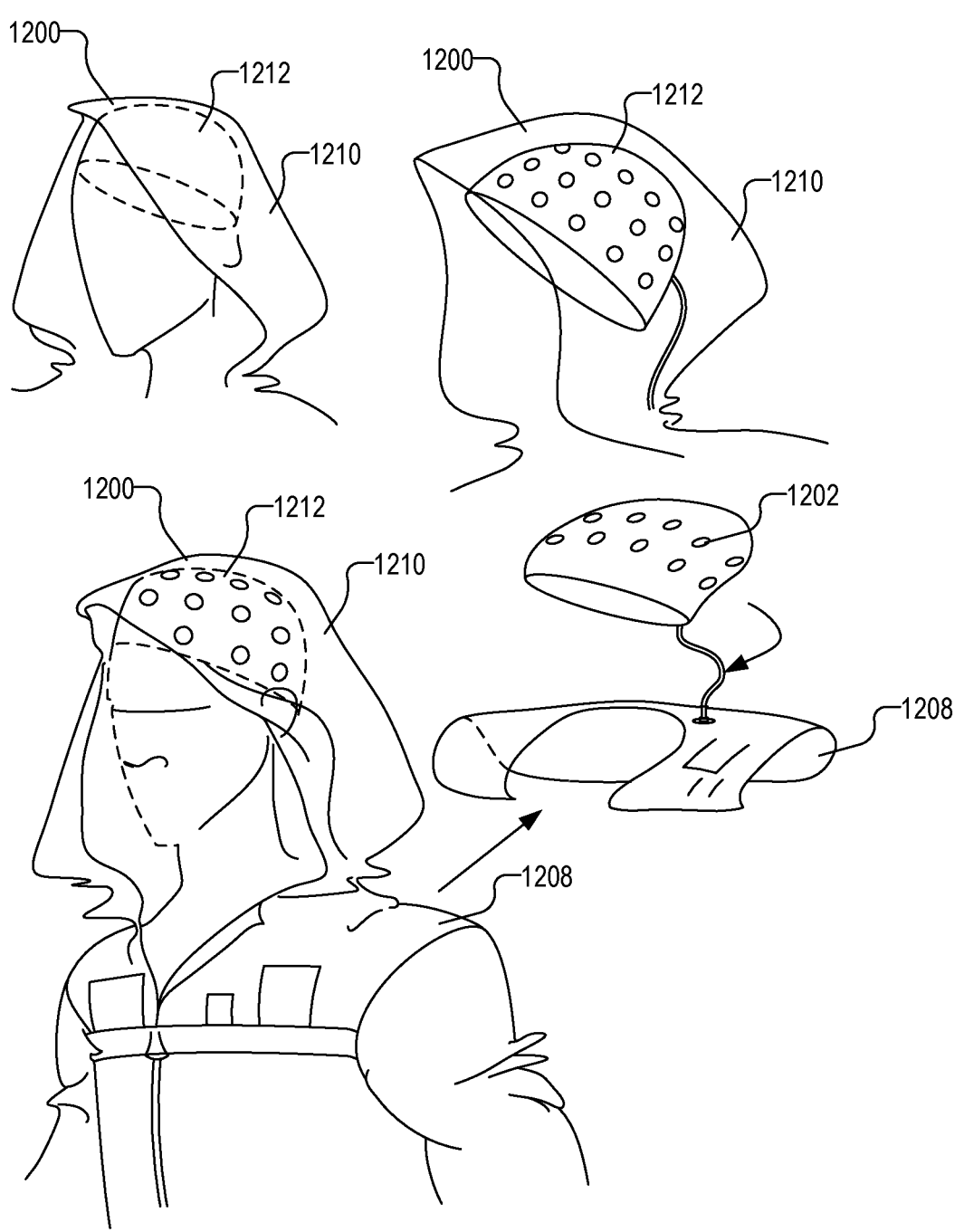

1208 in the form of a scarf that may contain or conceal a cable, battery, and/or hub. FIG. 16 illustrates additional embodiments of a wearable device 1200 in the form of a helmet with a one-piece scarf 1208 or two-piece scarf 1208-1. FIG. 17 illustrates an embodiment of a wearable device 1200 that includes a hood 1210 and a beanie 1212 which contains the modules 1202, as well as a wearable garment 1208 that may contain a battery or hub.

FIG. 18 illustrates an exemplary method 1800. While FIG. 18 illustrates exemplary operations according to one embodiment, other embodiments may omit, add to, reorder, and/or modify any of the operations shown in FIG. 18. One or more of the operations shown in FIG. 18 may be performed by any system described herein (e.g., optical measurement system 100 or brain interface system 500), any components included therein (e.g., wearable module 600), and/or any implementation thereof.

In operation 1802, a first light source housed within a housing of a wearable module emits a first light pulse toward an optical member housed within the housing. The first light pulse has a first wavelength. Operation 1802 may be performed in any of the ways described herein.

In operation 1804, a second light source housed within the housing emits a second light pulse toward the optical member. The second light pulse has a second wavelength that is different from the first wavelength. Operation 1804 may be performed in any of the ways described herein.

In operation 1806, the optical member directs the first light pulse and the second light pulse to a proximal end of a light guide included in the wearable module. Operation 1806 may be performed in any of the ways described herein.

In operation 1808, the light guide emits, from a distal end of the light guide, the first light pulse and the second light pulse toward a target within a body of a user of the wearable module. Operation 1808 may be performed in any of the ways described herein.

FIG. 19 illustrates an exemplary method 1900. While FIG. 19 illustrates exemplary operations according to one embodiment, other embodiments may omit, add to, reorder, and/or modify any of the operations shown in FIG. 19. One or more of the operations shown in FIG. 19 may be performed by any system described herein (e.g., optical measurement system 100 or brain interface system 500), any components included therein (e.g., wearable module 600), and/or any implementation thereof.

In operation 1902, a light guide included in a wearable module being worn by a user receives photons from at least one light pulse after the at least one light pulse is scattered by a target within a body of the user. Operation 1902 may be performed in any of the ways described herein.

In operation 1904, the light guide guides the photons to at least one time-resolved single photon photodetector housed within a housing of the wearable module. Operation 1904 may be performed in any of the ways described herein.

In operation 1906, the at least one time-resolved single photon photodetector detects the photons guided by the light guide. Operation 1906 may be performed in any of the ways described herein.

In some examples, a non-transitory computer-readable medium storing computer-readable instructions may be provided in accordance with the principles described herein. The instructions, when executed by a processor of a computing device, may direct the processor and/or computing device to perform one or more operations, including one or more of the operations described herein. Such instructions may be stored and/or transmitted using any of a variety of known computer-readable media.

A non-transitory computer-readable medium as referred to herein may include any non-transitory storage medium that participates in providing data (e.g., instructions) that may be read and/or executed by a computing device (e.g., by a processor of a computing device). For example, a non-transitory computer-readable medium may include, but is not limited to, any combination of non-volatile storage media and/or volatile storage media. Exemplary non-volatile storage media include, but are not limited to, read-only memory, flash memory, a solid-state drive, a magnetic storage device (e.g. a hard disk, a floppy disk, magnetic tape, etc.), ferroelectric random-access memory ("RAM"), and an optical disc (e.g., a compact disc, a digital video disc, a Blu-ray disc, etc.). Exemplary volatile storage media include, but are not limited to, RAM (e.g., dynamic RAM).

Figure 20:
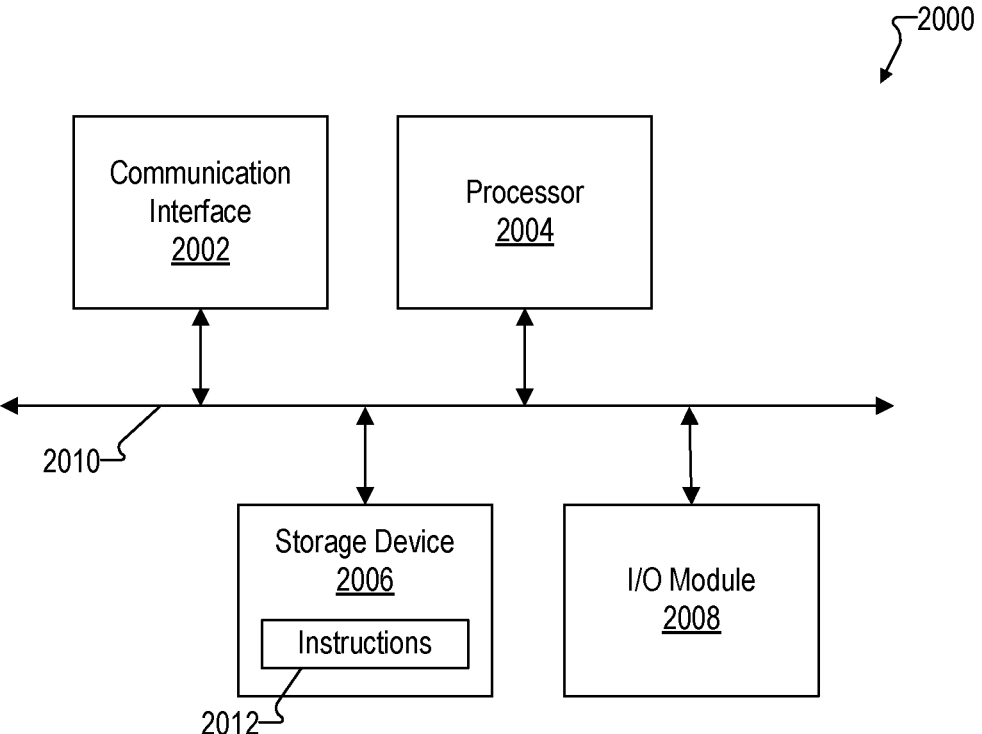
FIG. 20 illustrates an exemplary computing device.

FIG. 20 illustrates an exemplary computing device 2000 that may be specifically configured to perform one or more of the processes described herein. Any of the systems, units, computing devices, and/or other components described herein may be implemented by computing device 2000.

As shown in FIG. 20, computing device 2000 may include a communication interface 2002, a processor 2004, a storage device 2006, and an input/output ("I/O") module 2008 communicatively connected one to another via a communication infrastructure 2010. While an exemplary computing device 2000 is shown in FIG. 20, the components illustrated in FIG. 20 are not intended to be limiting. Additional or alternative components may be used in other embodiments. Components of computing device 2000 shown in FIG. 20 will now be described in additional detail.

Communication interface 2002 may be configured to communicate with one or more computing devices. Examples of communication interface 2002 include, without limitation, a wired network interface (such as a network interface card), a wireless network interface (such as a wireless network interface card), a modem, an audio/video connection, and any other suitable interface.

Processor 2004 generally represents any type or form of processing unit capable of processing data and/or interpreting, executing, and/or directing execution of one or more of the instructions, processes, and/or operations described herein. Processor 2004 may perform operations by executing computer-executable instructions 2012 (e.g., an application, software, code, and/or other executable data instance) stored in storage device 2006.

Storage device 2006 may include one or more data storage media, devices, or configurations and may employ any type, form, and combination of data storage media and/or device. For example, storage device 2006 may include, but is not limited to, any combination of the non-volatile media and/or volatile media described herein. Electronic data, including data described herein, may be temporarily and/or permanently stored in storage device 2006. For example, data representative of computer-executable instructions 2012 configured to direct processor 2004 to perform any of the operations described herein may be stored within storage device 2006. In some examples, data may be arranged in one or more databases residing within storage device 2006.

I/O module 2008 may include one or more I/O modules configured to receive user input and provide user output. I/O module 2008 may include any hardware, firmware, software, or combination thereof supportive of input and output capabilities. For example, I/O module 2008 may include hardware and/or software for capturing user input, including, but not limited to, a keyboard or keypad, a touchscreen component (e.g., touchscreen display), a receiver (e.g., an RF or infrared receiver), motion sensors, and/or one or more input buttons.

I/O module 2008 may include one or more devices for presenting output to a user, including, but not limited to, a graphics engine, a display (e.g., a display screen), one or more output drivers (e.g., display drivers), one or more audio speakers, and one or more audio drivers. In certain embodiments, I/O module 2008 is configured to provide graphical data to a display for presentation to a user. The graphical data may be representative of one or more graphical user interfaces and/or any other graphical content as may serve a particular implementation.

In the preceding description, various exemplary embodiments have been described with reference to the accompanying drawings. It will, however, be evident that various modifications and changes may be made thereto, and additional embodiments may be implemented, without departing from the scope of the invention as set forth in the claims that follow. For example, certain features of one embodiment described herein may be combined with or substituted for features of another embodiment described herein. The description and drawings are accordingly to be regarded in an illustrative rather than a restrictive sense.

What is claimed is:

1. An optical measurement system comprising:
a time-resolved single-photon photodetector;
a wearable module comprising:
    a housing including a top surface;
    a light guide including a distal end portion adapted to protrude from the top surface of the housing; and
    a spring member configured to bias the distal end portion of the light guide away from the top surface; and
a signal processing circuit;
wherein the light guide is configured to receive, at the distal end portion, photons from a light pulse scattered by a target within a body of a user and guide the received photons toward the photodetector; and
wherein the signal processing circuit is configured to:
    determine a temporal distribution of the photons detected by the photodetector, and
    generate a histogram based on the temporal distribution of the photons.

2. The optical measurement system of claim 1, wherein the photodetector is housed within the housing.

3. The optical measurement system of claim 1, wherein:
the wearable module further comprises at least one time-to-digital converter (TDC), and
the at least one TDC is configured to measure a time difference between an occurrence of the light pulse and an occurrence of an output pulse generated by the photodetector and indicating that the photodetector has detected a photon.

4. The optical measurement system of claim 1, wherein the signal processing circuit is housed in the housing.

5. The optical measurement system of claim 1, further comprising an additional housing separate from the housing, wherein the signal processing circuit is housed in the additional housing and communicatively coupled with the photodetector by way of a wired or wireless communication link.

6. The optical measurement system of claim 5, wherein the additional housing is wearable by a user.

7. The optical measurement system of claim 1, further comprising a head-mountable component configured to be worn on a head of the user, wherein the wearable module is included in the head-mountable component.

8. The optical measurement system of claim 7, wherein the head-mountable component comprises a plurality of wearable modules.

9. The optical measurement system of claim 1, wherein the target comprises a brain of the user.

10. The optical measurement system of claim 1, wherein the light guide is movable along an optical axis of the light guide.

11. The optical measurement system of claim 1, wherein the light guide is configured to be pressed toward the top surface by the body of the user when the wearable module is worn by the user.

12. The optical measurement system of claim 1, further comprising a light guide block,
wherein the light guide block includes a chamber and the light guide is disposed in the chamber.

13. The optical measurement system of claim 12, wherein the spring member is disposed in the chamber.

14. The optical measurement system of claim 12, wherein the light guide is movable within the chamber along a direction extending from a distal end of the chamber to a proximal end of the chamber.

15. The optical measurement system of claim 12, wherein:
    the housing comprises an upper housing and a lower housing, and
    the upper housing is implemented by the light guide block.

16. The optical measurement system of claim 1, wherein the wearable module further comprises a light-emitting light guide including a distal end portion configured to protrude from the top surface of the housing, the light-emitting light guide configured to emit, at the distal end portion, the photons toward the target; and
    an additional spring member configured to bias the distal end portion of the light-emitting light guide away from the top surface.

17. The optical measurement system of claim 16, further comprising a light source housed within the housing and configured to generate the photons.

18. The optical measurement system of claim 17, wherein the light source comprises one or more laser diodes.

19. The optical measurement system of claim 17, wherein the light-emitting light guide is movable relative to the light source.

20. The optical measurement system of claim 16, further comprising a plurality of light-receiving light guides, the plurality of light-receiving light guides including the light guide, wherein:
    each light-receiving light guide includes a distal end portion configured to protrude from the top surface of the housing;
    each light-receiving light guide is configured to receive, at the distal end portion, photons from the light pulse scattered by the target and guide the received photons toward the photodetector; and
    the distal end portion of each light-receiving light guide is biased away from the top surface of the housing.

21. The optical measurement system of claim 20, further comprising a plurality of spring members, wherein each spring member is configured to bias the distal end portion of a light-receiving light guide included in the plurality of light-receiving light guides away from the top surface of the housing.

22. The optical measurement system of claim 20, wherein an extent to which each light-receiving light guide of the plurality of light-receiving light guides protrudes from the top surface is independently adjustable such that, when the wearable module is worn by the user, each light-receiving light guide included in the plurality of light-receiving light guides is in physical contact with the body of the user.

23. The optical measurement system of claim 20, wherein a distance between each light-receiving light guide and the light-emitting light guide is fixed, when the wearable module is viewed in plan view.

\* \* \* \* \*